US006086876A

United States Patent [19]
Karp et al.

[11] Patent Number: 6,086,876
[45] Date of Patent: Jul. 11, 2000

[54] METHODS AND COMPOSITIONS FOR THE INHIBITION OF INTERLEUKIN-12 PRODUCTION

[75] Inventors: Christopher L. Karp, Lutherville, Md.; Giorgio Trinchieri; Maria Wysocka, both of Wynnewood, Pa.; Diane E. Griffin, Hunt Valley, Md.

[73] Assignees: The Wistar Insitute, Philadelphia, Pa.; Johns Hopkins University, Baltimore, Md.

[21] Appl. No.: 09/019,862

[22] Filed: Feb. 6, 1998

Related U.S. Application Data
[60] Provisional application No. 60/037,722, Feb. 7, 1997.

[51] Int. Cl.[7] .......................... A61K 39/395; C07K 16/28
[52] U.S. Cl. .................. 424/144.1; 424/85.2; 424/130.1; 424/133.1; 424/143.1; 424/152.1; 424/153.1; 424/173.1; 424/212.1; 530/388.7; 530/388.22; 530/389.6
[58] Field of Search .............................. 424/130.1, 133.1, 424/143.1, 152.1, 153.1, 173.1, 212.1, 85.2, 144.1; 530/388.7, 389.6, 388.22

[56] References Cited

U.S. PATENT DOCUMENTS

| 5,334,702 | 8/1994 | Greene ..................................... 530/323 |
| 5,573,764 | 11/1996 | Sykes et al. ........................... 424/85.2 |

FOREIGN PATENT DOCUMENTS

| WO91/18097 | 5/1991 | WIPO . |
| WO93/01201 | 7/1992 | WIPO . |
| WO94/17810 | 2/1994 | WIPO . |
| WO94/23744 | 4/1994 | WIPO . |

OTHER PUBLICATIONS

Kimball, John W. Introduction to immunology. Macmillan, New York. 1983, pp. 33–34, 114–115, 425.
Turco, S.J. "Intravenous Admixtures", Chapter 85, in, Remington's Pharmaceutical Sciences, 18th edition (Jun. 1990), Mack Pub. Co., Easton, Pennsylvania, p. 1570.
Aaby et al., 1993, J. Pediatr.122:904–908.
Adams et al., 1991, J. Immunol. 147:3005–3011.
Adorini et al., 1996, Res. Immunol. 146:645–651.
Andrews et al., 1985, Ann. Hum. Genet. 49:31–39.
Anguita et al., 1996, J. Clin. Invest. 97:1028–1034.
Arneborn et al., 1983, Infect. Immun. 39:29–37.
Azuma et al., 1995, Scandinavian J. Immunol. 42:202–208.
Baczko et al., 1992, Virology 190:469–474.
Barbas, 1995, Nature Medicine 1:837–839.
Burton et al., 1994, Adv. Immunol. 57:191–280.
Castro et al., 1995, J. Immunol. 155:2013–2019.
Chehimi et al., 1994, J. Exp. Med.179:1361–1366.
Cho et al., 1991, Clin. Exp. Immunol. 83:257–261.
Cohen 1993, Science 259:1691–1692.
Conlan et al., 1992, J. Leuk. Biol. 52:130–132.
Cranage et al., 1986, EMBO J. 5:3057–3063.
D'Andrea et al., 1992, J. Exp. Med. 176:1387–1398.
de Kruif et al. 1995, J. Mol. Biol. 248:97–105.

Dentener et al., 1993, J. Immunol. 151:4258–4265.
Dörig et al., 1993, Cell 75:295–305.
Durum et al., 1993, In "Fundamental Immunology", W. E. Paul, Ed., Raven Press Ltd. New York, pp. 801–835.
Esolen et al., 1993, J. Infect. Dis. 168:47–52.
Esolen et al., 1995, J. Virol. 69:3955–3958.
Fearon et al., 1995, Annu. Rev. Immunol. 13:127–149.
Fynan et al., 1993, Proc. Natl. Acad. Sci. 90:11478–11482.
Garenne et al., 1991, Lancet 338:903–907.
Gazzinelli et al., 1993, Proc. Natl. Acad. Sci. U.S.A. 90:6115–6119.
Gerlier et al., 1994, J. Gen. Virol.75:2163–2171.
Germann et al., 1995, Proc. Natl. Acad. Sci. USA 92:4823–4827.
Griffin et al., 1993, J. Infect. Dis.168:275–281.
Griffin et al., 1990, Clin. Exp. Immunol. 81:218–224.
Heinzel et al., 1993, J. Exp. Med. 177:1505–1509.
Hirsch et al., 1984, Clin. Immunol. Immunopathol. 31:1–12.
Hirsch et al., 1981, Clin. Immunol. Immunopathol. 21:341–350.
Holt et al., 1993, J. Infect. Dis.168:1087–1096.
Johnson et al., 1996, Infect. Immun. 64:1998–2003.
Kalli et al., 1991, J. Exp. Med. 174: 1451–1460.
Karp et al., 1993, J. Clin. Invest. 91:1644–1648.
Karp et al., 1996, Science 273:228–231.
Kay et al., 1997, Proc. Natl. Acad. Sci. USA 94:12744–12746.
Leonard et al., 1995, J. Exp. Med. 181:381–386.
Liszewski et al., 1991, Annu. Rev. Immunol. 9:431–455.
Malvoisin et al., 1994, J. Gen. Virol. 75:3603–3609.
Manchester et al., 1995, Proc. Natl. Acad. Sci. USA 92:2303–2307.
Manetti et al., 1995, Eur. J. Immunol. 25:2656–2660.
Marks et al., 1991, J. Mol. Biol. 222:581–597.
Marra et al., 1990, J. Immunol. 144:662–666.
Mayernik et al., 1984, J. Leuk. Biol. 36:551–557.
Mertz et al., 1994, J. Biol. Chem. 269:21322–21329.
Modlin et al., 1996, Res. Immunol. 146:526–531.
Moench et al., 1988, J. Infect. Dis. 158:433–442.
Moller et al., 1996, J. Immunol. 153:4952–4960.
Müller et al., 1995, J. Immunol. 155:4661–4668.
Naniche et al., 1993, J. Virol.67:6025–6032.
Neurath et al., 1995, J. Exp. Med. 182:1281–1290.
Neurath et al., 1996, J. Exp. Med. 183:2605–2616.
Nussbaum et al., 1995, J. Virol. 69:3341–3349.
Ooi et al., 1991, J. Exp. Med. 174:649–655.
Ozmen, et al., 1995, J. Virol. 69:8147–8150.
Rima et al., 1997, J. Gen. Virol. 76:1173–1180.

(List continued on next page.)

*Primary Examiner*—Elizabeth Kemmerer
*Assistant Examiner*—David S. Romeo
*Attorney, Agent, or Firm*—Akin, Gump, Strauss, Hauer & Feld, L.L.P.

[57] ABSTRACT

The invention includes compositions and methods for selective suppression of IL-12 production in a cell. Methods of treating a human having a disease associated with dysregulated IL-12 production are also provided.

12 Claims, 18 Drawing Sheets

OTHER PUBLICATIONS

Ross et al., 1993, Clin. Exp. Immunol. 92:181–184.
Scharton–Kersten et al., 1995, J. Exp. Med. 154:5320–5330.
Segal et al., 1996, J. Exp. Med. 184:771–775.
Seya et al., 1995, Immunol. 84:619–625.
Sypek et al., 1993, J. Exp. Med.177:1797–1802.
Tamashiro et al., 1987, Pediatr. Infect. Dis. J. 6:451–454.
Trembleau et al., 1995, J. Exp. Med. 181:817–821.
Trinchieri, et al., 1994, Blood, 84: 4008–4027.
Trinchieri, 1995, Ann. Rev. Immunol. 13:251–276.
Tripp et al., 1994, J. Immunol. 152:1883–1887.
Urban et al., 1996, J. Immunol.156:263–268.
Vainionpää et al., 1978, Acta. Pathol. Microbiol. Immunol. Scand. 86:379–385.
Via et al., 1994, J. Immunol. 153:4040–4047.
von Pirquet, 1908, Deutsch. Med. Wochenschr. 30:1297.
Wahl, 1981, In: Manual of Macrophage Methodology, Herscowitz et al., Eds. Marcel Dekker, Inc., New York and Basel, pp. 423–429.
Wahl et al., 1984, Cell. Immunol. 85:373–383.
Ward et al., 1993, Clin. Immunol. Immunopathol. 67:171–177.
Whistler et al., 1996, Virol. 220:480–484.
Whittle et al., 1978, J. Clin. Invest. 62:678–684.
Williamson et al., 1996, J. Immunol. 157:689–699.
Windhagen et al., 1995, J. Exp. Med. 182:1985–1996.
Wolff et al. 1991, Biotechniques 11:474–485.
Wysocki et al., 1995, Eur. J. Immunol. 25:672–676.
Zhang et al., 1994, J. Clin. Invest. 93:1733–1739.
Zhou et al., 1995, J. Immunol. 155:785–795.
Zurawski et al., 1994, Immunol. Today 15:19–26.
Zweiman et al., 1971, Int. Arch. All. Appl. Immunol.40:834–841.

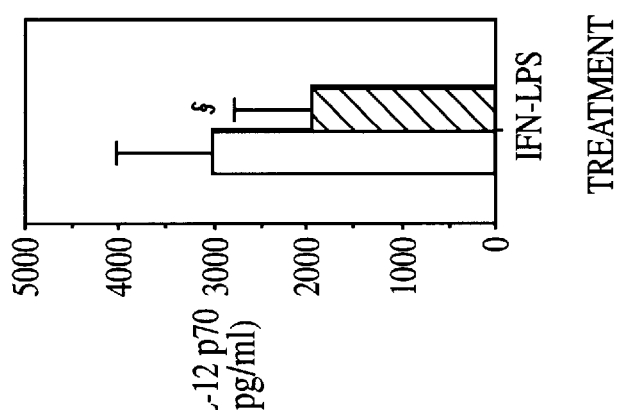
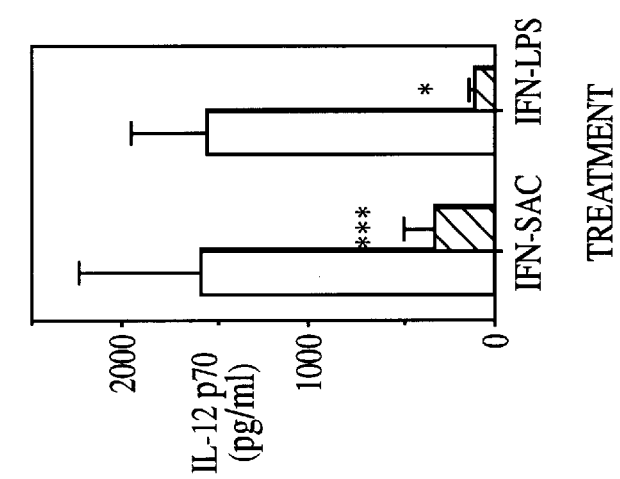
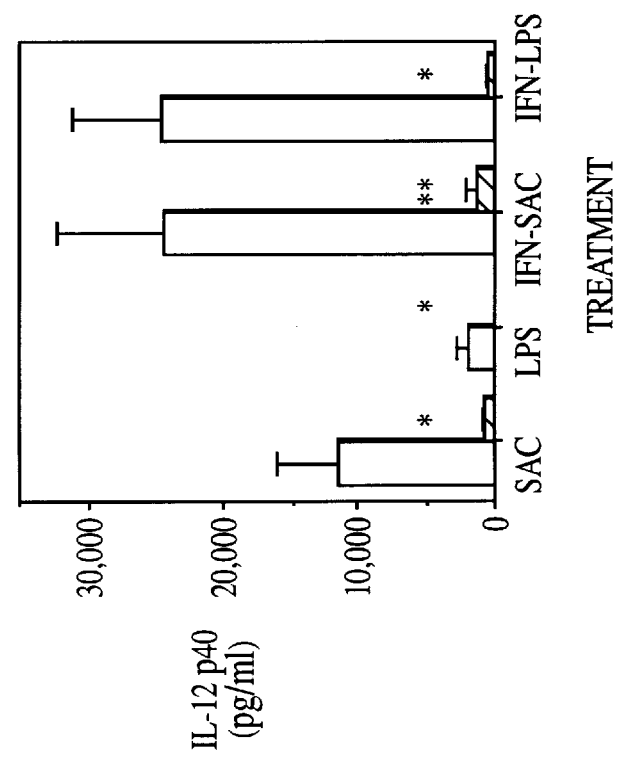
Fig. 1C
Fig. 1B
Fig. 1A

METHODS AND COMPOSITIONS FOR THE INHIBITION OF INTERLEUKIN-12 PRODUCTION

CROSS REFERENCE TO RELATED APPLICATIONS

This application claims priority under 35 U.S.C. § 119(e) to U.S. Provisional Application Ser. No. 60/037,722, filed on Feb. 7, 1997.

GOVERNMENT SUPPORT

This invention was supported in part using U.S. Government funds (National Institutes of Health, Grant Nos. AI01223, AI35149, AI23047, AI34412, CA20833, CA10815, and CA32898) and the U.S. Government may therefore have certain rights in the invention.

FIELD OF THE INVENTION

The present invention relates generally to pharmaceutical compositions and methods of use thereof in treating or preventing diseases related to the inappropriate activity of the immune response.

BACKGROUND OF THE INVENTION

IL-12 is a heterodimeric cytokine which provides a key link between the innate and acquired immune systems (Trinchieri, 1995, Ann. Rev. Immunol. 13:251). The functional heterodimer comprising IL-12, named p70, is composed of the covalently linked, glycosylated products of two separate genes: a heavy chain subunit named p40, whose expression is tightly regulated in cells which secrete the intact heterodimer, and a light chain subunit named p35, which is constitutively expressed at low levels in most cell types that have been studied.

Production of IL-12 in animals is stimulated in response to the presence of bacteria (e.g., *Staphylococcus aureus*), bacterial products (e.g., endotoxin/lipopolysaccharide (LPS)), protozoa (e.g., *Toxoplasma gondii*), viruses (e.g., mouse cytomegalovirus) and mimics of viral double stranded (ds) RNA replicative intermediates (e.g., polyinosinic acid:polycytidylic acid) (Trinchieri, et al., 1995, J. Virol. 69:1955); Manetti et al., 1995, Eur. J. Immunol. 25:2656).

IL-12 is critical for the development of cell-mediated immunity (CMI) in a mammal in that it is a potent inducer of IFN-γ production in T cells and NK cells, it is co-mitogenic for T cells and NK cells, it is required for the development of Th1 responses, it is necessary for DTH responses, and it is an enhancer of NK cell cytotoxicity (Trinchieri, et al., 1994, Blood, 84: 4008; Muller et al., 1995, J. Immunol. 155:4661). Monocytes are the principal producers of IL-12 in peripheral blood mononuclear cells (PBMC), and monocyte/macrophages are believed to be the principal IL-12 producing cells in vivo (Trinchieri et al., 1992, J. Exp. Med. 176:1387; Gazzinelli et al., 1993, Proc. Natl. Acad. Sci. U.S.A. 90:6115).

In the case of a number of viruses which perturb the CMI, monocyte-macrophages are prime target cells during natural infection with these viruses. Such viruses include measles virus (Esolen et al., 1993, J. Infect Dis. 169:47; Moench et al., 1988, J. Infect. Dis. 158:433). Infection with measles virus is accompanied by marked and prolonged abnormalities in the CMI response which are believed to contribute to the increased susceptibility to secondary infections in the mammal that account for most of the morbidity and mortality of the disease. Sensitization and expression of delayed-type hypersensitivity (DTH) responses are inhibited in vivo in an animal for several weeks following acute measles infection (von Pirquet, 1908, Deutsch. Med. Wochenschr. 30:1297; Tarnashiro et al., 1987, Pediatr. Infect. Dis. J. 6:451). In vitro, lymphoproliferative responses to antigen, recall antigen and mitogen are suppressed, and NK cell activity is markedly decreased (Whittle et al., 1978, J. Clin. Invest. 62:678; Arnebom et al., 1983, Infect. Immun. 39:29; Hirsch et al., 1984, Clin. Immunol. Immunopathol. 31:1; Griffin et al., 1990, Clin. Exp. Immunol. 81:218). There is additional in vivo and in vitro evidence of a type 2 polarization in cytokine responses during and following measles virus infection which is evidenced by the elevated production of IL-4 and decreased production of IL-2 and IFN-γ (Griffin et al., 1993, J. Infect. Dis.168:275). Immunization with live attenuated measles virus vaccine produces similar abnormalities in CMI (Hirsch et al., 1981, Clin. Immunol. Immunopathol. 21:341; Zweiman et al., 1971, Int. Arch. All. Appl. Immunol.40:834; Ward et al., 1993, Clin. Immunol. Immunopathol.67:171).

Vaccination of infants with a high-titer measles virus vaccine is associated with an increase in mortality suggesting that, similar to the situation during infection with wild-type infection, the alterations in CMI induced by infection with the vaccine strain may be of significant clinical importance (Garenne et al., 1991, Lancet 338:903; Aaby et al., 1993, J. Pediatr.122:904; Holt et al., 1993, J. Infect. Dis.168:1087). The mechanisms responsible for the marked suppression of CMI associated with measles virus infection remain obscure.

The receptor for measles virus is CD46. This protein is also known as membrane cofactor protein, a cell-surface member of the Regulators of Complement Activation (RCA) gene cluster (Naniche et al., 1993, J. Virol.67:6025; Dorig et al., 1993, Cell 75:295 1993). RCA family members control fluid phase and membrane amplification of complement activation at the pivotal C3 step and are related genetically, being tightly clustered on chromosome 1. RCA members are also related structurally, being composed of repeating motifs known as short consensus repeats (SCRs) consisting of about 60 amino acids with 4 invariant cysteines and 10–18 other highly conserved amino acids. These members are related functionally as well, in that they bind the complement activation products C3b and C4b (Naniche et al., 1993, J. Virol.67:6025; Dorig et al., 1993, Cell 75:295). Members of the RCA family of proteins include, among others, CD46, CD55, CD21, CD35 and CD59.

CD46 contains 4 SCRs. The binding site for measles virus hemagglutinin on CD46 involves SCRs 1 and 2. C3b binds to SCR's 3 and 4 and C4b binds to SCR's 2, 3 and 4 (Gerlier et al., 1994, J. Gen. Virol.75:2163; Nussbaum et al., 1995, J. Virol. 69:3341; Manchester et al., 1995, Proc. Natl. Acad. Sci. USA 92:2302; Adams et al., 1991, J. Immunol. 147:3005). The role of CD46 in complement activation and in complement-mediated disorders is discussed in WO91/18097. Further, anti-CD46 antibodies have been used to block the action of complement regulatory proteins in order to prevent the degradation of complement (Azuma et al., 1995, Scandinavian J. Immunol. 42:202–208). Since the Azuma et al. study involved the use of anti-CD46 antibodies to mediate complement lysis of human tumor cells which were present in a mouse, it was not possible to examine the overall effect of administration of anti-CD46 antibodies on the immune system of the mouse because mouse cells do not react with these antibodies and to date, no mouse homolog of human CD46 has been identified. The use of anti-CD46 monoclonal antibodies to block measles virus infection has been reported (Seya et al., 1995, Immunol. 84:619–625). However, the mechanism by which this inhibition was effected has not been disclosed.

Complement receptor 3 (CR3) is a member of the β2 integrins family of heterodimeric cell surface proteins, is composed of two polypeptide chains, α and β, and is a complement receptor present on monocytes/macrophages, neutrophils, and NK cells. CR3 has two binding domains: a lectin domain, which mediates the binding of several bacteria, intracellular parasites, zymosan, β-glucan, I-CAM, fibrinogen, CD14/LPS, and an I domain, which binds iC3b (Ross et al., 1993, Clin. Exp. Immunol. 92:181–184). Previously published reports established that administration of antibody against CR3 to animals suppressed the delayed type hypersensitivity (DTH) reaction and exacerbated infection with *Listeria monocytogenes* or *Toxoplasma gondii* (Conlan et al., 1992, J. Leuk. Biol. 52:130–132; Johnson et al., 1996, Infect Immun. 64:1998–2003).

Mononuclear cells obtained from EHV patients are markedly impaired in their ability to produce IL-12 (Chehimi et al., 1994, J. Exp. Med.179:1361), suggesting the possibility that such aberrant IL-12 production has a pathogenetic role in the immunodeficiency associated with HIV infection.

IL-12 is critical for the generation of CMI responses. CMI responses are critical for clearance of and immunity to a wide variety of pathogens (Castro et al., 1995, J. Immunol. 155:2013; Tripp et al., 1994, J. Immunol. 152:1883; Heinzel et al., 1993, J. Exp. Med. 177:1505; Sypek et al., 1993, J. Exp. Med. 177:1797; Scharton-Kersten et al., 1995, J. Exp. Med. 154:5320; Urban et al., 1996, J. Immunol.156:263; Zhou et al., 1995, J. Immunol. 155:785; Zhang et al., 1994, J. Clin. Invest.93:1733; Modlin et al., 1996, Res. Immunol. 146:526). However, CMI responses may also be pathogenic. There is clear evidence that inappropriate CMI responses accompanied by dysregulated type 1 cytokine expression and/or pathological DTH responses, are integral to the development of several immunologically-mediated disorders. A pathogenic role for IL-12 has been implicated in several of these conditions, including rheumatoid arthritis (Germann et al., 1995, Proc. Natl. Acad. Sci. USA 92:4823), multiple sclerosis (Windhagen et al., 1995, J. Exp. Med. 182:1985; Leonard et al., 1995, J. Exp. Med. 181:381; Segal et al., 1996, J. Exp. Med. 184:771), graft-versus-host disease (Via et al., 1994, J. Immunol. 153:4040; Williamson et al., 1996, J. Immunol. 157:689), diabetes mellitus (Trembleau et al., 1995, J. Exp. Med. 181:817; Adorini et al., 1996, Res. Immunol. 146:645), sarcoidosis (Moller et al., 1996, J. lmnunol. 153:4952), granulomatous colitis (Neurath et al., 1995, J. Exp. Med. 182:1281; Neurath et al., 1996, J. Exp. Med. 183:2605), systemic lupus erythematosus and Crohn's disease.

There remains a need in the art for a method for suppressing unwanted CMI responses in certain disease states. There also remains a need for the development of agents which function to suppress unwanted CMI responses in certain disease states. The present invention satisfies this need.

SUMMARY OF THE INVENTION

The invention relates to a method of treating a human having a disease characterized by dysregulated IL-12 production. The method comprises administering to the human an anti-complement receptor protein ligand suspended in a pharmaceutically acceptable carrier in an amount sufficient to selectively suppress IL12 production in the human, wherein the ligand does not bind IL-12 receptor protein.

In one aspect, the ligand is selected from the group consisting of an anti-CD46 ligand and an anti-CR3 ligand.

In another aspect, the ligand is an isolated protein or an isolated polypeptide.

In preferred embodiments, the ligand is selected from the group consisting of a polyclonal antibody, a monoclonal antibody, a synthetic antibody, a chimeric antibody and a humanized antibody.

In yet other preferred embodiments, when the ligand is an anti-CD46 ligand, the anti-CD46 ligand is selected from the group consisting of an anti-CD46 antibody, C3b, C4b, and measles virus hemagglutinin. Preferably, the anti-CD46 ligand is an anti-CD46 antibody.

In other preferred embodiments, when the ligand is an anti-CR3 ligand, the anti-CR3 ligand is selected form the group consisting of an anti-CR3 antibody, zymosan, β-glucan, I-CAM, fibrinogen, CD14/LPS, and iC3b. Preferably, the anti-CR3 ligand is an anti-CR3 antibody.

In another aspect of the invention, the ligand is administered to the human in the form of an isolated DNA encoding and capable of expressing the ligand. Preferably, the DNA is formulated in a viral or a non-viral vector. When the vector is a viral vector, the viral vector is selected from the group consisting of a recombinant vaccinia virus, a recombinant adenovirus, a recombinant retrovirus, a recombinant adeno-associated virus and a recombinant avian pox virus. When the vector is a non-viral vector, the non-viral vector is selected from the group consisting of a liposome and a polyamine conjugated DNA.

In another aspect of the invention, the disease is inappropriate or pathological delayed-type hypersensitivity. Preferably, the delayed-type hypersensitivity is associated with an organ-specific autoimmune disease. More preferably, the disease to be treated is selected from the group consisting of rheumatoid arthritis, multiple sclerosis, graft-versus-host disease, diabetes mellitus, sarcoidosis, granulomatous colitis, systemic lupus erythematosus and Crohn's disease. The disease may also be a bacterial disease. When the disease is a bacterial disease, the bacterial disease is selected from the group consisting of Lyme's disease and endotoxic shock.

In another preferred embodiment, the anti-complement receptor protein ligand is administered to the human in an amount between about 1 ng/kg and about 100 mg/kg of patient body weight. Also preferred when the anti-complement receptor ligand is an anti-CD46 ligand, the anti-CD46 ligand is administered to the human in an amount between about 15 micrograms to about 80 micrograms of ligand per kg of patient body weight.

In yet another preferred embodiment, the pharmaceutically acceptable carrier is physiological saline.

The invention also relates to a method of treating a human having a disease characterized by dysregulated IL-12 production. The method comprises administering to the human a pharmaceutically effective amount of an isolated nucleic acid encoding an anti-complement receptor protein ligand, wherein the nucleic expresses the ligand in vivo in an amount sufficient to selectively suppress IL-12 production in the human.

In preferred embodiments, the anti-complement receptor protein ligand is selected from the group consisting of an anti-CD46 ligand and an anti-CR3 ligand. When the anti-complement receptor ligand is an anti-CD46 ligand, the anti-CD46 ligand is selected from the group consisting of an anti-CD46 antibody C3b, C4b and measles virus hemagglutinin. When the anti-complement receptor ligand is an anti-CR3 ligand, the anti-CR3 ligand is selected from the group consisting of an anti-CR3 antibody, zymosan, β-glucan, I-CAM, fibrinogen, CD14/LPS, and iC3b.

Also included in the invention is a method of identifiing a ligand capable of binding to a cognate receptor protein, wherein when the ligand is bound to the protein, production of IL-12 in a human is suppressed. The method comprises incubating a population of IL-12 producing cells in the presence of an inducer of IL-12 and in the presence or absence of a test ligand, and measuring the level of IL-12 production in the cells, wherein a lower level of IL-12 production in the cells in the presence of the test ligand compared with the level of EL-12 production in the cells in the absence of the test ligand, is an indication that the test ligand is capable of binding to the cognate receptor protein thereby suppressing IL-12 production.

In one aspect of this aspect of the invention, the cells are selected from the group consisting of monocytes and neutrophils.

The invention further includes a ligand useful for suppression of IL-12 production in a human made according to the recited method of identifing a ligand.

BRIEF DESCRIPTION OF THE DRAWINGS

FIG. 1A is a graph depicting measles virus-induced inhibition of IL12 p40 production (n=7–11) by primary human monocytes. Mock-infected cultures are illustrated by the white bars; measles virus-infected cultures are illustrated by the black bars. Monocytes were stimulated with *Staphylococcus aureus* Cowan strain 1 (SAC), lipopolysaccharide (LPS), interferon gamma (IFN-γ) plus SAC, or IFN-γ plus LPS, as indicated. Values shown are means plus standard errors. Statistical analysis of paired log-transformed data was performed using the paired Students's t test: *P<0.0001, **P=0.0001, in comparison with mock infection.

FIG. 1B is a graph similar to that of FIG. 1A depicting IL-12 p70 production (n=7–9). The symbols are as in the description of FIG. 1A and ***P=0.0009 in comparison with mock infection.

FIG. 1C is a graph similar to that of FIG. 1A depicting IL-12 p70 production after UV inactivation of virus prior to infection of cells (n=3). The symbols are as in the description of FIG. 1A and §P=0.029 in comparison with mock infection.

DETAILED DESCRIPTION OF THE INVENTION

Figure 2B:
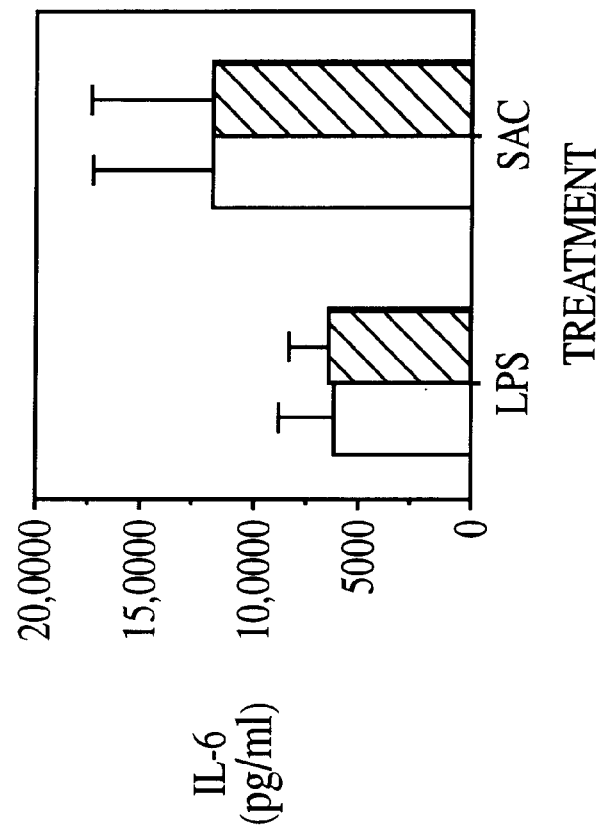
FIG. 2B is a graph similar to that of FIG. 2A depicting the production of interleukin-6 (IL-6) under the same conditions as the experiment shovn in FIG. 2A. The symbols used are the same as in the description of FIG. 2A.
Figure 2A:
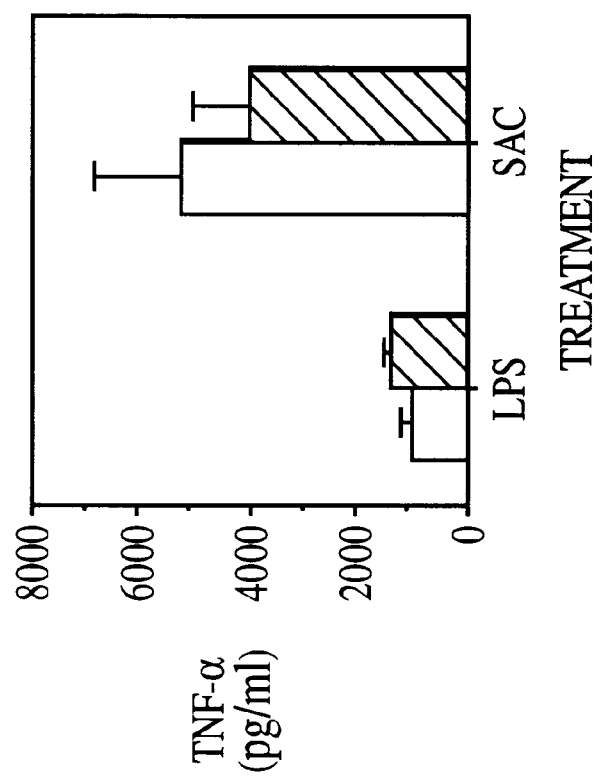
FIG. 2A is a graph depicting the production of tumor necrosis factor alpha (TNF-α) by measles virus-infected monocytes in response to stimulation with LPS or SAC. Values shown are means plus standard errors of mock-infected (white bars) and measles virus-infected (black bars) monocyte cultures (n=3–6). * P<0.05.
Figure 2D:
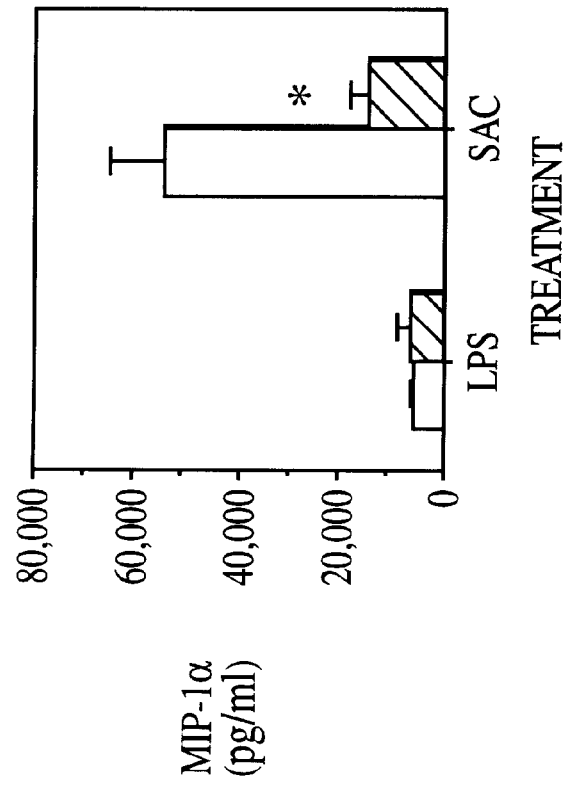
FIG. 2D is a graph similar to that of FIG. 2A depicting the production of macrophage inflammatory protein-1α(MIP-1α) under the same conditions as the experiment shown in FIG. 2A. The symbols are the same as in the description of FIG. 2A.

The present invention is based upon the discovery that certain agents are capable of inhibiting production of IL-12 when administered to a mammal. Since dysregulated IL-12 production in a mammal is associated with a variety of diseases, inhibition of IL-12 production is of benefit in alleviating or ablating such diseases.

The present invention provides a method of treating a variety of disorders in a mammal characterized by dysregulated, physiologically abnormal, aberrant IL-12 production and/or overproduction of IL-12. The mammal is preferably a human. As discussed herein, IL-12 is critical for the generation of cell mediated immune (CMI) responses, which in some instances are critical for clearance of and immunity to a wide variety of pathogens. Thus, the method of the invention is useful for the treatment of a variety of diseases in a mammal caused by pathogenic organisms. In addition, the method of the invention is usefull for the treatment of any other disease states which are associated with physiologically abnormal production, generally overproduction, of IL-12. Such diseases include those characterized by inappropriate CMI responses, and/or dysregulated type 1 cytokine expression, and/or pathological DTH responses.

By the term "dysregulated IL-12 production" as used herein, is meant, physiologically abnormal, aberrant production of IL-12, or overproduction of IL-12 in a diseased mammal, which is production is significantly different from that in an otherwise identical, but non-diseased mammal. Generally, the level of production of IL-12 in the diseased mammal is higher than the level of IL-12 production in the nondiseased mammal. The term "significantly different" as used herein should be construed to mean that the level is sufficient to contribute to the disease state of the mammal. By way of example, certain disease states recited herein are known to be accompanied by overproduction of IL-12 in a mammal. According to the definition provided herein, in such mammals, the level of production of IL-12 is considered to be significantly higher than that in an otherwise identical, but non-diseased mammal, since overproduction of IL-12 in the mammal contributes to the disease state. In addition, the term "dysregulated production of IL-12" should be construed to include situations where downregulation of IL-12 production in a diseased mammal serves to alleviate a disease state in the mammal, irrespective of the initial IL-12 levels in the mammal. In other words, the method of the invention should be construed to include instances wherein a diseased mammal may express normal levels of IL-12, but would benefit from suppression of such levels to below normal levels.

Diseases which may be treated according to the method of the invention include, but are not limited to, those which have as a component of the disease an inappropriate or pathological delayed-type hypersensitivity, a condition which is often associated with an organ-specific autoimmune disease. These diseases include, but are not limited to, rheumatoid arthritis, multiple sclerosis, graft-versus-host disease, diabetes mellitus, sarcoidosis, granulomatous colitis, systemic lupus erythematosus and Crohn's disease. Overproduction of IL-12 is also responsible for morbidity and mortality associated with diseases caused by pathogenic organisms. Thus, other diseases which are suitable for treatment using the method of the invention include, but are not limited to, Lyme disease induced by infection with *Borrelia burgdorferi* (Anguita et al., 1996, J. Clin. Invest. 97:1028–1034), endotoxic shock induced by systemic bacterial infections (Kubin et al., 1995, Eur. J. Immunol. 25:672–676) and septic shock.

The present invention is based upon the observation that during the interplay between measles virus infection and IL-12, a mechanism for use in treating disorders caused by dysregulated, physiologically abnormal, aberrant IL-12 production and/or overproduction of IL-12 became apparent. As described in detail herein, infection of primary human monocytes with measles virus specifically downregulated IL-12 production (Example 1). When CD46, a complement regulatory protein which is the cellular receptor for measles virus, was cross-linked with antibody, monocyte IL-12 production was similarly downregulated (Example 4). This observation provides a plausible mechanism for measles virus-induced immunosuppression. Furthermore, an endogenous ligand for CD46 named C3b, also potently suppressed production of IL-12 (Examples 4 and 5).

In Example 6, there is provided data which establish that CR3 also plays a role in the regulation of IL-12 production by cells. These data further establish that anti-CR3 ligands are useful for suppression of IL-12 production by cells. In summary therefore, certain complement receptor proteins play a key role in production of IL-12 in cells. Ligands which bind independently to at least two complement receptor proteins, CD46 and CR3, are capable of suppressing production of IL-12 when so bound. The data described herein thus establish that ligands directed against CD46, CR3 and likely other complement receptor proteins, are useful for suppression of IL-12 production in cells.

The invention should therefore be construed to include any ligand that is currently either known or is heretofore unknown, which when bound to a complement receptor protein, effects suppression of IL-12 production in a cell expressing the receptor protein.

By the term "ligand" as used herein, is meant any natuaal or synthetic composition or compound which is capable of specifically binding to its cognate receptor protein, and when so bound, activates a biological fuinction of the cognate receptor protein such that suppression of IL-12 production is effected. By way of example, an antibody which specifically binds to CD46 and inhibits the function thereof, is termed an "anti-CD46 ligand." In this context, CD46 is the "cognate receptor protein" for the ligand. Similarly, by way of example, since C3b binds CD46 and effects suppression of IL-12 production as the data presented herein establish, C3b is a ligand for CD46 and CD46 is a cognate receptor protein for C3b under the definition used herein.

The term "ligand" as used herein, is meant to specifically exclude an anti-IL-12 receptor ligand, that is a ligand which specifically binds to IL-12 receptor protein. A "ligand" as used herein, is one which does not bind to the IL-12 receptor, but rather binds to a non-IL-12 receptor protein to effect suppression of IL-12 production.

By the term "anti-complement receptor protein ligand" as used herein, is meant any natural or synthetic composition or compound which is capable of binding to a complement receptor protein found on the cell surface, which binding effects suppression of IL-12 production in the cell.

By the term "anti-CD46 ligand" as used herein, is meant any natural or synthetic composition or compound which is capable of binding to a CD46 binding site found on the cell surface, which binding effects suppression of IL-12 production in the cell. The term should be construed to include any and all ligands which perform this function and should be particularly construed to include anti-CD46 antibodies, C3b, C4b and measles virus hemagglutinin. Preferably, the C3b and the C4b are polymerized C3b and polymnerized C4b.

By the term "anti-CR3 ligand" as used herein, is meant any natural or synthetic composition or compound which is capable of binding to a CR3 binding site found on the cell surface, which binding effects suppression of IL-12 production in the cell. The term should particularly be construed to include anti-CR3 antibodies, iC3b, β-glucan, zymosan, fibrinogen, ICAM-1 and CD14. Preferably, the anti-CR3 ligand is either an antibody or is iC3b.

The invention includes a method of selectively suppressing inappropriate, physiologically abnormal IL-12 production in patients exhibiting disease characteristics such as, for instance, pathogenic CMI responses. The method involves administering a pharmaceutically effective amount of a ligand which is capable of binding to its cognate receptor protein, wherein when the ligand binds its cognate receptor protein, IL-12 production is suppressed.

By the term "selectively suppressing IL-12 production" as used herein, is meant that IL-12 production is suppressed in the absence of any appreciable suppression of other monokines essential for a physiologically normal CMI response.

The invention should not be construed to be limited to the specific ligands and respective cognate receptor proteins disclosed in the Examples presented herein. Rather, the invention should be construed to include any presently known or heretofore unknown ligands which have the effect of suppression IL-12 production in cells. It is a simple matter, upon reading the present disclosure, to use the IL-12 suppression assays described in the Examples to identify additional ligands and their cognate receptor proteins, which ligands are capable of suppressing IL-12 production in cells. Thus, while preferred ligands for use in the methods of the invention are selected from the group consisting of anti-CD46 and anti-CR3 ligands, yet other usefuil ligands may be identified using the protocols described herein. The most preferred ligand for use in the methods of the invention is an anti-CD46 ligand.

To identify a ligand capable of suppressing IL-12 production in cells, a population of cells, for example, monocytes or neutrophils, which normally produce IL-12, is obtained. The cells are induced to produce IL-12 and a test ligand is added. The level of IL-12 production in the cells following the addition of the test ligand is assessed and is compared with the level of IL-12 production in cells to which the test ligand was not added. A lower level of IL-12 production in cells in the presence of the test ligand, compared with the level of IL-12 production in cells in the absence of the test ligand, is an indication that the ligand is one which is capable of suppressing IL-12 production. Additional assays which definitively establish that the test ligand is capable of selectively suppressing IL-12 production in cells may then be conducted following the protocols provided herein in the Examples section.

The ligand for use in the method of the invention may be any natural or synthetic composition or compound which when bound to its cognate receptor protein, effects the selective suppression of production of IL-12. Thus, the ligand may be a protein, a peptide or a small molecule. The ligand may be administered to a cell as is, that is, as an isolated protein, an isolated peptide, a small molecule, or it may be administered to the cell in the form of an isolated nucleic acid sequence encoding the ligand.

By the term "isolated nucleic acid", as used herein, refers to a nucleic acid sequence, a DNA or an RNA or fragment thereof wvhich has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector; into an autonomously replicating plasmid or virus; or into the genomic DNA of a prok-aryote or eukaryote; or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequences.

In other related aspects, the invention includes vectors which contain such isolated nucleic acid and which are preferably capable of directing expression of the protein encoded by the nucleic acid in a vector-containing cell; and cells containing such vectors, either eukaryotic cells or prokaryotic cells, preferably eukaryotic cells.

The isolated nucleic acid of the invention should be construed to include an RNA or a DNA sequence encoding a ligand of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

By the terms "isolated peptide" or "isolated protein," as used herein, is meant a peptide or protein which has been substantially separated from the components, e.g,. DNA, RNA, other proteins and peptides, carbohydrates and lipids, which naturally accompany the protein or peptide in the cell. The terms isolated peptide and protein may be construed to include a peptide or protein which is expressed and/or secreted from a cell comprising an isolated nucleic acid.

The present invention also provides for analogs of proteins or peptides which comprise a ligand as defined herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating ernymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Desirable isolated protein or isolated peptide ligands include antibodies which bind to the desired cognate receptor protein. Because the preferred ligand of the invention is an anti-CD46 ligand, the discussion which follows regarding the generation of ligands and nucleic acid encoding the same, uses as an example, an anti-CD46 ligand. However, as noted herein, the invention should in no way be construed as being limited solely to an anti-CD46 ligand, but should be construed to include any and all ligands which fall into the definition of a ligand as described herein Thus, the description which follows is applicable to any suitable ligand, including the preferred ligands which include an anti-CD46 ligand and an anti-CR3 ligand.

The ligand of the invention may be an antibody. The antibody may be any type of antibody including, but not limited to, a polyclonal antibody, a monoclonal antibody, a synthetic antibody, a chimeric antibody, a humanized antibody, and the like. Other anti-complement receptor protein ligands, for example, an anti-CD46 ligand, include proteins which are not antibodies, such as measles virus hemagglutinin Polymerized C3b, and polymerized C4b are also anti-CD46 ligands. C3 activation fragments and C3b dimers are known ligands for CD46 (Liszewski et al., 1991, Annu. Rev. Immunol. 9:431; Gerlier et al., 1994, J. Gen. Virol. 75:2163; Nussbaum et al., 1995, J. Virol. 69:3341; Manchester et al., 1995, Proc. Natl. Acad. Sci. USA 92:2303; Adams et al., 1991, J. Immunol. 147:3005).

Antibody technology is described in Harlow et al. (1988, In: Antibodies, A Laboratory Manual, Cold Spring Harbor, N.Y.). Polyclonal antibodies directed against, for example, CD46 may be made by immunizing any suitable animal and obtaining immune serum from the animal at selected intervals following immunization.

Monoclonal antibodies directed against full length or peptide fragments of, for example, CD46, may be prepared using any well known monoclonal antibody preparation procedures, such as those described, for example, in Harlow et al. (supra). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. in Immunol. 12(3,4):125–168) and the references cited therein. Further, the antibody may be "humanized" using the technology described in Wright et al., (supra) and in the references cited therein.

To generate a phage antibody library, a cDNA library is first obtained from mRNA which is isolated from cells, e.g., the hybridoma, which express the desired protein to be expressed on the phage surface, e.g. the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifing immunoglobulin genes. The procedures for making a bacteriophage library comprising heterologous DNA are well known in the art and are described, for example, in Sambrook et al. (1989, Molecular Cloning. A Laboratory Manual, Cold Spring Harbor, N.Y.) and in Ausubel et al. (Ausubel et al., 1993, Current Protocols in Molecular Biology, Green & Wiley, New York).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged irnmunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks etal.(1991, J. Mol. Biol.222:581–597). Panningofphagesogeneratedforthe isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837–839; de Kruif et al. 1995, J. Mol. Biol. 248:97–105).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art The invention thus includes an isolated DNA encoding a complement receptor protein ligand or DNA encoding a portion of the ligand, which when the ligand is, for example, an antibody, the antibody is itself specific for its cognate complement receptor protein, or for fragments thereof.

To isolate DNA encoding an antibody, for example, DNA is extracted from antibody expressing phage obtained as described herein. Such extraction techniques are well known in the art and are described, for example, in Sambrook et al. (supra) and in Ausubel et al. (supra).

By the term "scFv/phage" are used herein, is meant a phage particle which expresses the Fv portion of an antibody as a single chain.

The invention should be construed to include other complement receptor protein-binding ligands which are either known or are heretofore unknown, which are, or will be designed to bind to a complement receptor protein and which are useful for controlling production of IL-12 by cells.

Another form of ligand, for example, an anti-CD46 ligand, includes a nucleic acid sequence which encodes the anti-CD46 ligand and which is associated with promoter/regulatory sequences which can direct expression of the anti-CD46 ligand in vivo. For a discussion of this technology, see, for example, Cohen (1993, Science 259:1691–1692), Fynan et al. (1993, Proc. Natl. Acad. Sci. 90:11478–11482) and Wolff et al. (1991, Biotechniques 11:474–485) which describe similar the use of naked DNA as a therapeutic agent. For example, a plasmid containing suitable promoter/regulatory sequences operably linked to a DNA sequence encoding an anti-CD46 ligand, may be directly administered to a patient using the technology described in the aforementioned references.

As used herein, the term "promoter/regulatory sequence" means a DNA sequence which is required for tissue-specific, organ specific, or other specific (such as inducible, etc) expression of a gene operably linked to the promoter/regulator sequence. In some instances, this sequence may be the core promoter sequence and in other instances, this sequence may also include an enhancer sequence and other regulatory elements which are required for expression of the gene in the desired specific manner.

By describing two nucleic acid sequences as "operably linked" as used herein, is meant that a single-stranded or double-stranded nucleic acid moiety comprises each of the two nucleic acid sequences and that the two sequences are arranged within the nucleic acid moiety in such a manner that at least one of the two nucleic acid sequences is able to exert a physiological effect by which it is characterized upon the other.

Alternatively, the promoter/enhancer sequence operably linked to DNA encoding, for example, an anti-CD46 ligand, may be contained within a vector, which vector is administered to the patient. The vector may be a viral vector which is suitable as a delivery vehicle for delivery of the anti-CD46 ligand DNA to the patient, or the Ivector may be a non-viral vector which is suitable for the same purpose. Examples of viral and non-viral vectors for delivery of DNA to cells and tissues are well known in the art and are described, for example, in (Ma et al., 1997, Proc. Natl. Acad. Sci. USA 94:12744–12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057–3063; International Patent Application No. WO94/17810, published Aug. 18, 1994; International Patent Application No. WO94/23744, published Oct. 27, 1994). Examples of non-viral vectors include, but are not limited to, liposomes, polyarnine derivatives of DNA, and the like.

The identity, selection and means for obtaining a desired anti-complement receptor protein ligand useful for treatment of a disease characterized by dysregulated or inappropriate IL-12 production (such as that associated with pathogenic CMI responses), may be performed by the skilled artisan using conventional technology when in possession of the present invention. For example, there are a variety of anti-CD46 and anti-CR3 monoclonal antibodies which are commercially available that are likely anti-CD46 ligands suitable for use in the methods of the invention. Further, polymerized complement fragments may be readily prepared in the laboratory using conventional methods (Kalli et al., 1991, J. Exp. Med. 174: 1451). Methods for production of recombinant measles virus hemagglutinin are also described in the literature (Malvoisin and Wild, 1994, J. Gen. Virol. 75:3603–3609).

Other anti-complement receptor protein ligands may include, but are not limited to, isolated proteins and isolated polypeptides and isolated nucleic acid sequences encoding the same. Isolated proteins and peptides having anti-complement receptor protein ligand activity and isolated nucleic acids encoding the same, may be chemically synthesized by conventional methods known in the art, or they may be purchased for a commercial source if available. In one embodiment of the invention, the anti-complement receptor protein ligand, being a protein, a peptide or a nucleic acid, may be produced using recombinant techniques in vitro in sufficiently large quantities for use in a therapeutic composition for use in treating diseases associated with dysregulated, physiologically abnormal, aberrant IL-12 production and/or overproduction of IL-12. In addition, a recombinant virus vector comprising DNA encoding the desired anti-complement receptor protein ligand may be prepared using conventional recombinant DNA technology procedures.

The ligand useful in the methods of the invention may be a small molecule, a peptidometic, and the like, which ligand binds to a desired cognate receptor protein thereby effecting suppression of IL-12 production. Once in possession of the present invention, it is within the skill of the ordinary artisan to identify the contact points between the ligand and the desired cognate receptor protein, which contact points are essential for binding of these molecules together to effect suppression of IL12 production. Thus, it is also within the skill of the artisan to design specific peptidometics which bind to, for example, CD46, and effect suppression of IL-12 production. The invention should be construed to include such peptidometics. The technology of the development of peptidometics is described, for example, in PCT/US93/01201 and U.S. Pat. No. 5,334,702.

As noted herein, the identification of a heretofore unknown anti-complement receptor protein ligand may be accomplished using any of the IL-12 synthesis assays described herein in the Examples. Essentially, a culture of monocytes, neutrophils or other IL-12 producing cells is obtained and IL-12 production is induced therein using any one of several available bacterial inducers. Following a period of induction, the test compound is added to an aliquot of the cells. An inhibitor of IL-12 production, for example, the presently discovered anti-CD46 ligand, is added to another aliquot of cells as a positive control. Incubation of yet another aliquot of cells is allowed to continue in the absence of any further additions. These latter cells serve as a negative control. The level of IL-12 production is measured in all aliquots of cells. A higher level of inhibition of IL-12 production in cells incubated in the presence of the test compound compared with the level of inhibition of IL-12 production in cells iincubated in the absence of the test compound is an indication that the test compound is an anti-complement receptor protein ligand. Additional experiments may then be performed, as described herein, to definitively identify the test compound as an anti-complement receptor protein ligand. Such experiments include binding assays to assess binding of the test compound to the cognate complement receptor protein, and the like, as described in the Examples presented herein.

The anti-complement receptor protein ligand of the invention may be formulated in a pharmaceutical composition which is suitable for administration of the ligand to a human patient. It will be appreciated that the precise formulation and dosage amounts will vary depending upon any number of factors, including, but not limited to, the type and severity of the disease to be treated, the route of administration, the age and overall health of the individual, the nature of the ligand, etc. However, the preparation of a pharmaceutically acceptable composition having an appropriate pH, isotonicity, stability and other characteristics is within the skill of the art Pharmaceutical compositions are described in the art, for example, in Remigton's Pharmaceutical Sciences (Genaro ed., 1985, Mack Publishing Co., Easton, Pa.).

As used herein, the term "pharrnaceutically-acceptable carrier" means a chemical composition with which an appropriate anti-complement receptor protein ligand, may be combined and which, following the combination, can be used to administer the ligand to a patient.

The amount of the anti-complement receptor protein ligand composition administered, whether it is administered as protein or as nucleic acid, is sufficient to selectively suppress IL-12 production in the patient without adversely suppressing production of other cytokines. Such selective suppression permits the re-establishment of a physiologically normal balance of IL-12 in the patient The pharmaceutical compositions useful for practicing the invention may be administered to deliver a dose of between about 1 ng/kg and about 100 mg/kg of patient body weight. Suitable amounts of the anti-complement receptor protein ligands for administration include doses which are high enough to have an IL-12 suppressive effect which re-establishes a normal IL-12 expression level in the patient, and yet are low enough so as to ensure that production of other monokines is not unduly adversely affected. When the anti-complement receptor protein ligand is a protein or peptide, a preferred dosage range is from about 15 to about 80 μg of protein or peptide per kg of patient body weight. More preferred dosages are the lower end of the stated range. When the anti-complement receptor protein ligand is administered in the form of DNA encoding the same contained within a recombinant virus vector, a dosage of between about $10^2$ and about $10^{11}$ plaque forming units of virus per kg of patient body weight may be used. When naked DNA encoding the anti-complement receptor protein ligand is to be administered as the pharmaceutical composition, a dosage of between about 20 μg about several mg of DNA per kg of patient body weight may be used.

In the practice of the methods of the invention, a composition containing an anti-complement receptor protein ligand is administered to a patient in a sufficient amount to suppress IL-12 production and to aid in re-establishing a physiologically normal state or amount of IL-12, without adversely affecting the essential expression of other cytokines. Patients to be treated include those which exhibit pathogenic CMI responses that are the result of, or are governed by dysregulated, physiologically abnormal, aberrant IL-12 production and/or overproduction of IL-12 in the patient.

The frequency of administration of an anti-complement receptor protein ligand to a patient will also vary depending on several factors including, but not limited to, the type and severity of the disease to be treated, the route of administration, the age and overall health of the individual, the nature of the ligand, etc. It is contemplated that the frequency of administration of the ligand to the patient may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate anti-complement receptor protein ligand, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate anti-complement receptor protein ligand to a patient according to the methods of the invention.

An anti-complement receptor protein ligands may be administered in conjunction with other compounds which are used to treat diseases associated with dysregulated, physiologically abnormal, aberrant IL-12 production and/or overproduction of IL-12. Such compounds include, but are not limited to, steroids, cytotoxic compounds, and the like. The choice of which additional compound to administer will vary depending upon any number of the same types of factors that govern the selection of dosage and administration frequency of the anti-complement receptor protein ligand. Selection of these types of compounds for use in conjunction with an anti-complement receptor protein ligand for practice of the method of the invention is well within the skill of those in the art.

The invention will be further described by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The data presented in the Examples section provides evidence that ligands which bind to cognate complement receptor proteins are capable of suppressing IL-12 production in cells which express the receptor protein.

Examples

Example 1

Measles Virus-Induced Inhibition of IL-12 Production by Primary Human Monocytes

Given the close match between the abnormalities of cellular immune function seen in measles and the known functions of IL-12, the following experiment was performed to examine the observation that measles virus infection downregulates the production of IL-12.

Human monocytes obtained from normal volunteers were isolated by countercurrent elutriation (Wahl et al., 184, Cell. Immunol. 85:373; Mertz et al., 1994, J. Biol. Chem. 269:21322). The elutriated monocytes were mock infected or were infected with the Vero cell-derived, wild-type Edmonston strain of measles virus under nonadherent conditions (Bellini et al., 1996, Virol. 220:480–484). Other measles virus strains which were tested in addition to wild-type Edmonston included a Finnish wild-type isolate (Vainionpaa et al., 1978, Acta. Pathol. Microbiol. Immunol. Scand. 86:379), as well as JM and Chicago-1 (Esolen et al., 1995, J. Virol. 69:3955–3958; Baczko et al., 1992, Virology 190:469–474; Rima et al., 1997, J. Gen. Virol. 76:1173).

Following infection, monocytes were then allowed to adhere to plastic, and were subsequently cultured in DMEM supplemented with 10% fetal bovine serum (Gibco) at a density of $2\times10^6$ cells/ml (1 ml/data point) in 24-well plates (Costar). Isolation and culture of the cells was performed under LPS-free conditions.

All cell culture reagents were LPS-free to the limits of detection of the Limulus amebocyte lysate assay (6–12.5 pg/ml) (BioWhittaker). The recombinant N-terminal fragment of bactericidal permeability inducing protein (rBPI; XOMA Corporation) which, at 5 μg/ml, has an LPS-binding capacity of>10 ng/ml (Marra et al., 1990, J. Immunol. 144: 662; Dentener et al., 1993, J. Immunol. 151:4258; Ooi et al., 1991, J. Exp. Med. 174:649) was employed in studies using reagents (antibodies, complement) which have measurable LPS contamination. At experimental dilutions, all such reagents contained considerably <10 ng/ml of LPS.

After 48–60 hours in culture, monocytes were secondarily stimulated with bacterial inducers of IL-12 production, i.e., with LPS 1 μg/ml (E. coli serotype 0127: B8; Sigma) or S. aureus Cowan strain 1 (SAC) 0.0075% (Calbiochem), wherein the cells were either prestimulated or were not prestimulated with IFN-γ at a concentration of 300 U/ml (Pharmingen) for 18 hours. At 24 hours following secondary stimulation, cell-free culture supernatants were harvested and the levels of various cytokines in the supernatants were assessed.

Levels of IL-12 p40 and p70 were assessed using specific radioimmunoassays (RIAs) as described (Kerp et al., 1996, Science 273:228–231). IL-12 p40 was measured using the monoclonal antibodies (MAbs) C 11.79 and C8.6 for capture and detection of IL-12 p40, respectively; p70 was measured using the MAb 20C2 for both capture and detection. Both RIAs have a sensitivity of 10 pg/ml.

The results of this experiment are shown in FIGS. 1A through 1C. Statistical analysis of log-transformed data was performed using the Student's t test (P<0.0001, P=0.0001, P=0.029 or P=0.0009 for the comparison of mock with measles virus infection as indicated in the figures). In the absence of stimulation, there was no detectable production of IL-12.

Infection of primary monocytes with measles virus dramatically downregulated the stimulated production of IL-12 both at the level of the highly regulated p40 subunit and at the level of the functional p70 heterodimer (See FIGS. 1A–1C). The suppression of IL-12 was stimulus-independent, occurring whether LPS or S. aureus (Cowan strain 1 [SAC]) was used alone (FIG. 1A), or whether these compounds were used following preincubation of the cells with IFN-γ (FIGS. 1A–1B). For example, in LPS-stimulated cultures, measles virus infection resulted in a 26.8-fold mean decrease in p40 production (FIG. 1A); in SAC-stimulated cultures, measles virus infection resulted in a 23-fold mean decrease in p40 secretion (FIG. 1A). In the case of IFN-γ/LPS-stimulated cultures, measles virus infection resulted in a 78.1-fold mean decrease in p40 production (FIG. 1A); and, in FN-γ/LPS-stimulated cultures, measles virus infection resulted in a 36.8-fold mean decrease in p70 production (FIG. 1B). Measles virus infection resulted in 27.8-fold and 20.5 fold mean decreases in IFN-γ/SAC stimulated production of p40 (P=0.0001) and p70 (P=0.0009), respectively. This suppression was also not narrowly strain-specific, as several different wild-type isolates of measles virus down-regulated monocytic production of IL-12 similarly.

The marked suppression of IL-12 production induced by measles virus occurred despite the fact that only a few monocytes were productively infected with the virus. Analysis performed using both indirect immunofluorescence to detect measles virus hemagglutinin (MV-H) and infectious center assays to directly detect virus, indicated that less than 3% of the monocytes were productively infected at the time of secondary stimulation.

Example 2

Characterization of Proteins Produced by Measles Virus Infected Cells

To establish that the observed inhibition of IL-12 production was not the result of a generalized failure of monocyte fumction due to non-specific effects of viral parasitism, the production of other proinflammatory cytokines and chemolines by measles virus infected cells was examined.

Mock or measles virus infected human monocytes were stimulated with SAC or LPS as described in Example 1, and the production of TNF-α, IL-6, MIP-1α and MIP-1β was measured. Measurement of TNF-α and IL-6 was performed by ELISA (Pharmingen); ELISA measurement of MIP-1α and MIP-1β was conducted as previously described (Liszewski et al., 1991, Annu. Rev. Immunol. 9: 431).

Figure 2C:
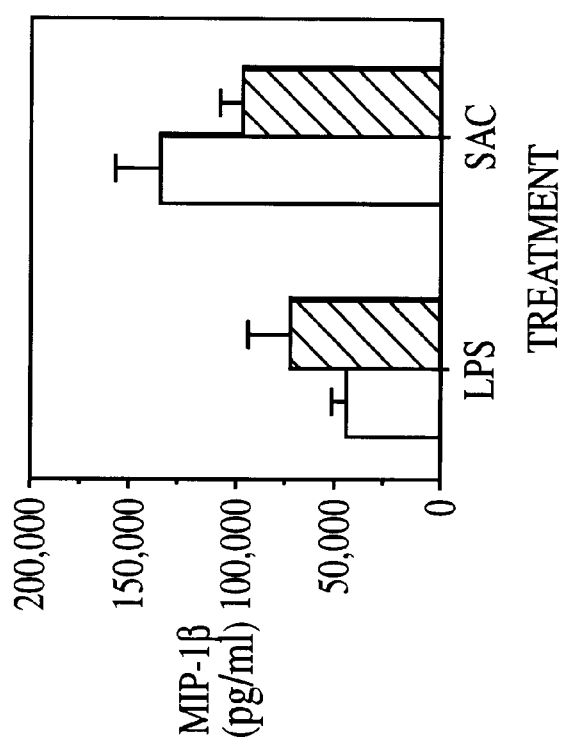
FIG. 2C is a graph similar to that of FIG. 2A depicting the production of macrophage inflammatory protein-1β(MIP-1β) under the same conditions as the experiment shown in FIG. 2A. The symbols are the same as in the description of FIG. 2A.

The results of these experiments are illustrated in FIGS. 2A through 2D. Measles virus infection did not alter the stimulated production of TNF-α (FIG. 2A), IL-6 (FIG. 2B) or MIP-1β (FIG. 2C). The SAC-stimulated secretion of MIP-1α was mildly suppressed by virus infection (FIG. 2D) in that measles virus infection of cells resulted in a 4-fold mean decrease in SAC-stimulated MIP-1α production (P<0.05).

IL-6 secretion was induced by measles virus infection alone (P=0.021; mean production of 171 pg/ml). This was the only analyzed cytokine whose production was detectable in the absence of LPS- or SAC-stimulation.

The effect of virus infection on the stimulated production of IL-1β in these cells was highly variable, but the overall level of IL-1β production was minimal as expected in monocytes which are cultured in vitro for more than 24–48 hours (Mayernik et al., 1984, J. Leuk. Biol. 36:551 (1984).

Example 3
Lack of Involvement of Known Monocyte-Derived Endogenous Inhibitors of IL-12 in Measles Virus-Induced Suppression of IL-12 Production Known endogenous inhibitors of IL-12 production include IL-10, TGF-β, IL-4, IL-13, and PGE2 (Zurawski et al., 1994, Immunol. Today 15:19; Durum et al., 1993, In "Fundamental Immunology", W. E. Paul, Ed., Raven Press Ltd. New York, pp. 801–833). All of these agents are known to suppress monocyte production of proinflammatory cytokines. Thus, it was expected that they would not be involved in measles virus-induced IL-12 suppression. The following experiments were performed to assess the involvement, if any, of these cytokines in measles virus induced suppression of IL-12 production.

IL-10 production by stimulated monocytes

Figure 3B:
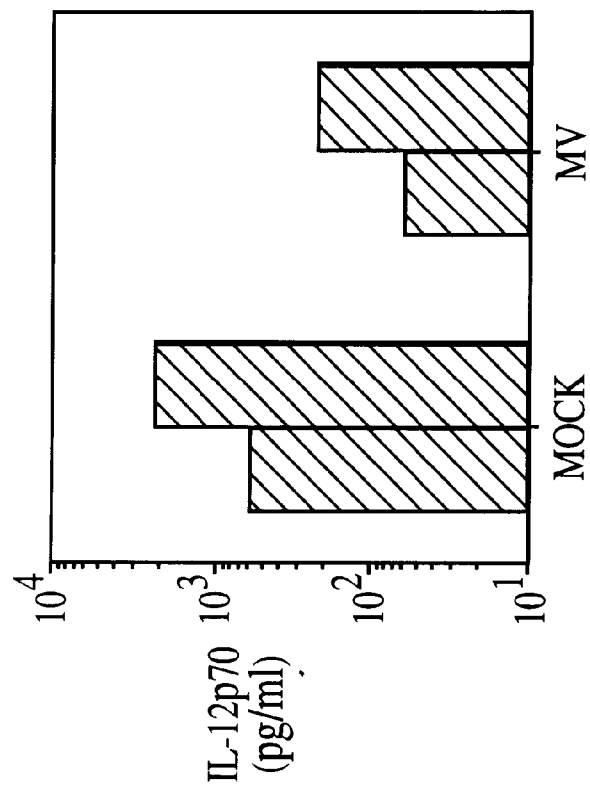
FIG. 3B is a graph depicting IL-12 p70 production in mock-infected or measles virus infected human monocytes stimulated with IFN-γ/LPS in the presence of 1 μg/ml JES3-9D7 neutralizing anti-IL-10 monoclonal antibody (dark hatching) or R59-40 antibody isotype control monoclonal (light hatching).
Figure 3A:
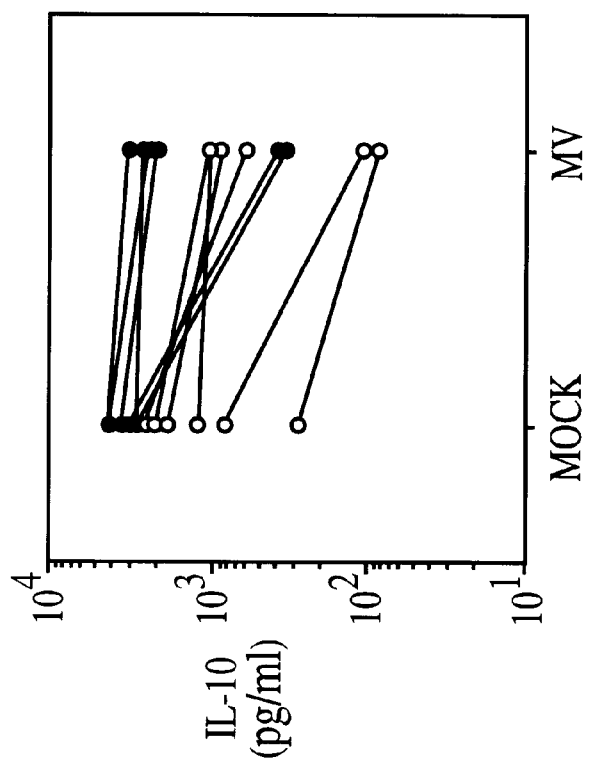
FIG. 3A is a graph depicting the production of IL-10 in response to stimulation of mock-infected or measles virus infected human monocytes with SAC (filled symbols) or LPS (open symbols) as described in Example 3. Each pair of depicted values represents monocytes obtained from a single donor.

Measles virus or mock infected human monocytes were stimulated with LPS or SAC as described in Example 1. IL-10 measurement was performed using an ELISA (Pharmingen). The results of this experiment are shown in FIG. 3A. Essentially, measles virus infection induced a 4-fold mean decrease in IL-10 production following LPS stimulation (P=0.005), and infection did not significantly alter IL-10 secretion induced by SAC stimulation (closed symbols).

Effect of IL-10 neutralization on the stimulated production of p70

Measles virus- or mock-infected monocytes were stimulated with IFN-γ/LPS in the presence of 1 μg/ml JES3–9D7 neutralizing anti-IL-10 MAb or R59-40 antibody isotype control MAb (both antibodies were obtained from Pharmingen). The results of one experiment which is representative of a total of five experiments, is shown in FIG. 3B. Neutralization of IL-10 resulted in similar changes in p70 production in both mock- and measles virus-infected monocyte cultures (3.8- and 3.7-fold increases, respectively). The use of IL-10 neutralizing antibodies increased the production of IL-12 similarly in both infected and uninfected monocyte cultures. These data establish that IL-10 does not play a role in the specific inhibition of IL-12 production effected by measles virus infection.

Lack of effect of TGF-β neutralization on IFN-γ/LPS-stimulated p70 production

Figure 3D:
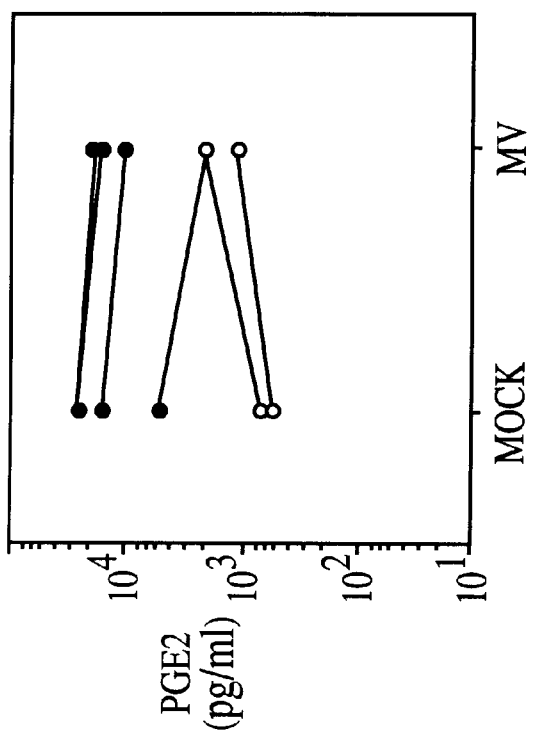
FIG. 3D is a graph depicting PGE2 production in mock-infected or measles virus infected human monocytes stimulated with SAC-(filled symbols) or LPS (open symbols) as in the description of FIG. 3A.
Figure 3C:
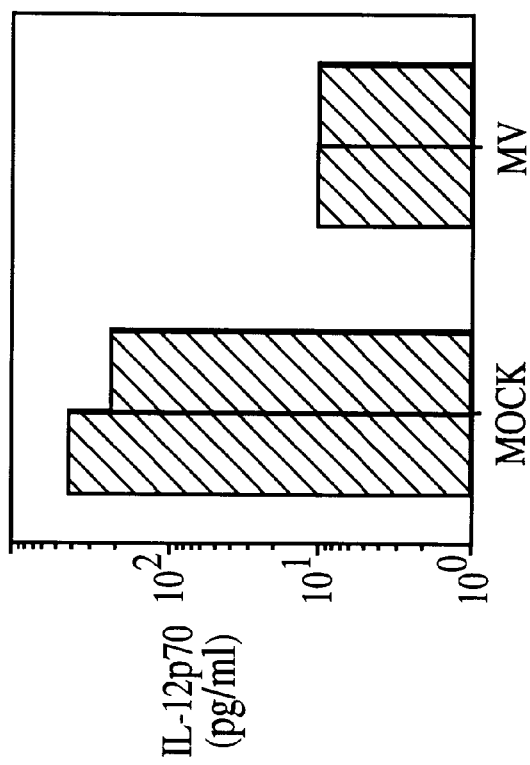
FIG. 3C is a graph depicting IL-12 p70 production in mock-infected or measles virus infected human monocytes stimulated with IFN-γ/LPS in the presence of neutralizing anti-TGF-β rabbit polyclonal (dark hatching) or isotype control (light hatching) antibodies.

Measles virus- or mock-infected monocytes were stimulated with IFN-γ/LPS in the presence of 5 μg/ml of neutralizig anti-TGF-β rabbit polyclonal or isotype control antibodies (both from R & D Systems) in a manner to that just described. The results of an experiment which is representative of a total of three experiments, are shown in FIG. 3C. Similar results were obtained using a neutralizing MAb anti-TGF-β (Genzyme) at a concentration of 5 or 30 μg/ml (in two experiments), suggesting that neutralization of TGF-β had no effect on IL-12 production.

PGE2 production by SAC- or LPS-stimulated monocytes

Human monocytes were infected with measles virus, wherein the cells were stimulated with LPS or SAC was performed as described in Example 1. PGE2 measurement conducted using RIA as described (Wahl, 1981, In: Manual of Macrophage Methodology, Herscowitz et al., Eds. Marcel Dekker, Inc., New York and Basel, pp. 423–429). According to the results shown in FIG. 3D, measles virus infection did not significantly alter PGE2 secretion in these cells. LPS- or SAC-stimulated PGE2 levels were not altered in infected compared with mock infected monocytes.

IL-4 and IL-13 production

IL-4 and IL-13 are primarily products of T cells, thus, they were not expected to play a role in suppression of measles virus induced IL-12 suppression in monocytes. However, given the possibility of low-level contamination of the elutriated monocytes with T cells, the production of these cytokines in monocytes was investigated.

Neither IL-4 protein nor IL-13 mRNA was detectable using an ELISA or using a RT-PCR assay. Levels of IL-4 were measured using an ELISA having a sensitivity of 10–20 pg/ml (Pharmingen). Levels of IL-13 were measured using a RT-PCR assay at 40 cycles (Karp et al., 1993, J. Clin. Invest. 91:1644).

Example 4
Suppression of IL-12 Production by Anti-CD46 Ligands

Given the lack of a demonstrable role for known endogenous soluble inhibitors of IL-12 in measles virus induced IL-12 suppression in monocytes, a direct interaction between measles virus and its cellular receptor was examined for the effect it may have on this phenomenon Suppression of IL-12 by anti-CD46 ligands To address the question of the involvement of CD46 in measles virus-related suppression of IL-12 production in monocytes, CD46 was cross-linked on the surface of monocytes with one of three different MAbs: 1) GB24 (courtesy of J. Atkinson), a MAb that blocks complement binding to SCRs 3 and 4 of CD46; 2) TRA-2-10 (courtesy of J. Atkinson), a MAb specific for SCRs 1 and 2 which blocks binding of compounds to CD46; and 3) J4-48 (Immunotech, Inc.), a MAb specific for SCRs 1 and 2 which fails to block measles virus binding to CD46 (see, e.g., Manchester et al., 1995, Proc. Natl. Acad. Sci. U.S.A. 92:2303; Dorig et al., 1993, Cell 75:295; Cho et al., 1991, Clin. Exp. Immunol. 83:257; Andrews et al., 1985, Ann. Hum. Genet. 49:31–39).

Monocytes were stimulated with IFN-γ/SAC or IFN-γ/LPS following preincubation with the selected anti-CD46 MAb or an isotype control anti-V3 MAb. The MAbs were ascites-derived antibodies employed at a final dilution of 1:333.

The results of these experiments are shown in FIGS. 4A–4D. Anti-CD46 GB24 MAb treatment of cells resulted in a 22.3-fold mean decrease in IFN-γ/SAC-stimulated p70 production and a 81.3-fold mean decrease in IFN-γ/LPS-stimulated p70 production (P=0.003 and P=0.049, respectively). MAb GB24 is known to block complement binding to SCRs 3 and 4 of CD46. Preincubation of cells with J4-48 resulted in a 14.7-fold (P=0.006) and a 29-fold (P=0.021) mean decrease in IFN-γ/SAC- and IFN-γ/LPS-stimulated p70 production, respectively. Preincubation of cells with TRA-2-10 MAb resulted in a 4.5-fold (P=0.024)

and a 4.6-fold (P=0.024) mean decrease in IFN-γ/SAC- and IFN-γ/LPS-stimulated p70 production, respectively.

Figure 5A:
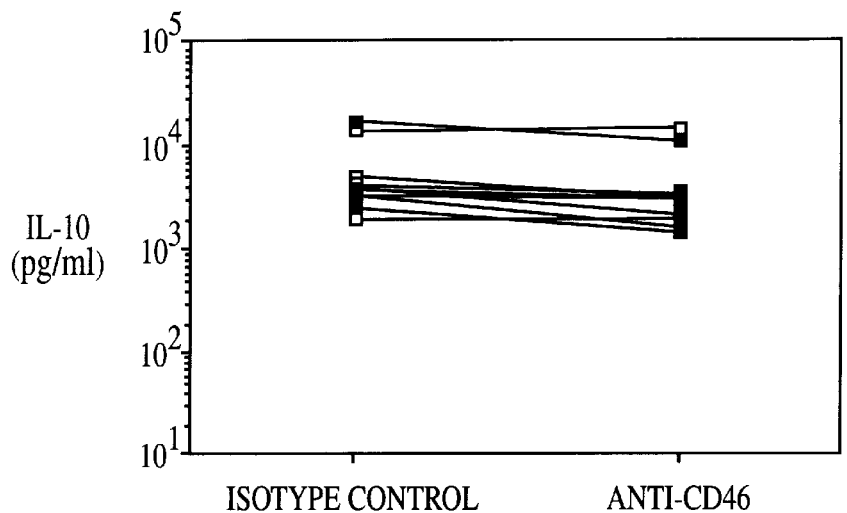
FIG. 5A is a graph depicting the specificity of suppression of SAC-stimulated IL-12 production by anti-CD46 antibodies as assessed by the lack of suppression of IL-10. Paired values are samples obtained from individual donors which samples were pre-incubated with J4-48 (filled square), GB24 (open square), or TRA-2-10 anti-CD46 (filled circle) as indicated in the description of FIG. 4A. N=4–7 for each antibody and cytokine.
Figure 5B:
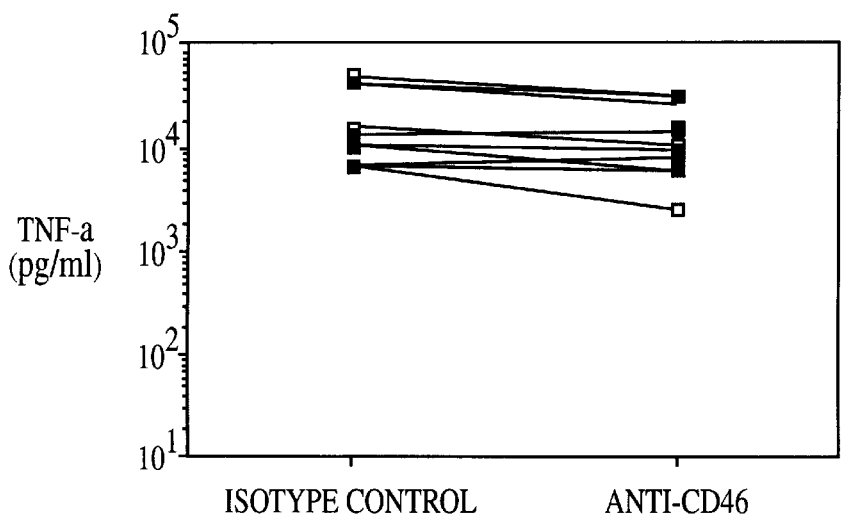
FIG. 5B is a graph similar to that of FIG. 5A, depicting the lack of suppression of TNF-α production by anti-CD46 antibodies when compared with SAC-stimulated IL-12 production. The symbols are as indicated in the description of FIG. 5A.
Figure 5C:
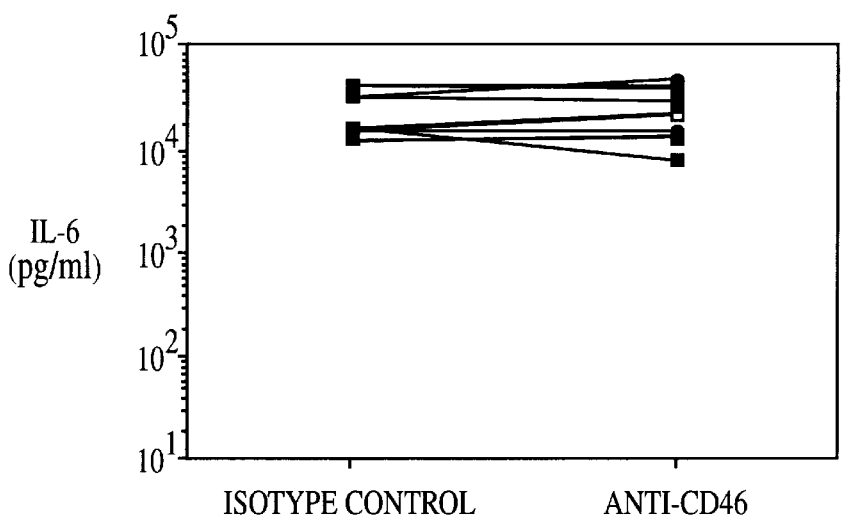
FIG. 5C is a graph similar to that of FIG. 5A, depicting the lack of suppression of IL-6 by anti-CD46 antibodies when compared with SAC-stimulated IL-12 production. The symbols are as indicated in the description of FIG. 5A.

In each instance, the MAbs resulted in a dramatic suppression of IL-12 production (FIGS. 4A–4D). Importantly, the monokine profiles of stimulated, anti-CD46-treated monocytes were similar to those of measles virus infected monocytes in that there was observed a marked suppression of IL-12 (FIGS. 4A–4D), and unaltered production of IL-10, TNF-α and IL-6 (FIGS. 5AC).

Inhibition of IL-12 Production By Inactivated Measles Virus

Treatment of ultraviolet (UV)-inactivated measles virus inhibited monocyte secretion of IL-12 (FIG. 1C), demonstrating that productive infection of monocytes with this virus is not necessary for downregulation of IL-12 downregulation.

Taken together, these studies suggest that binding of measles virus hemagglutinin to CD46 on the surface of monocytes is the key event in mediating downreguiation of IL-12 production by these cells.

Dose-dependent suppression of IL-12 by dimerzed C3b (pC3b)

Figure 4A:
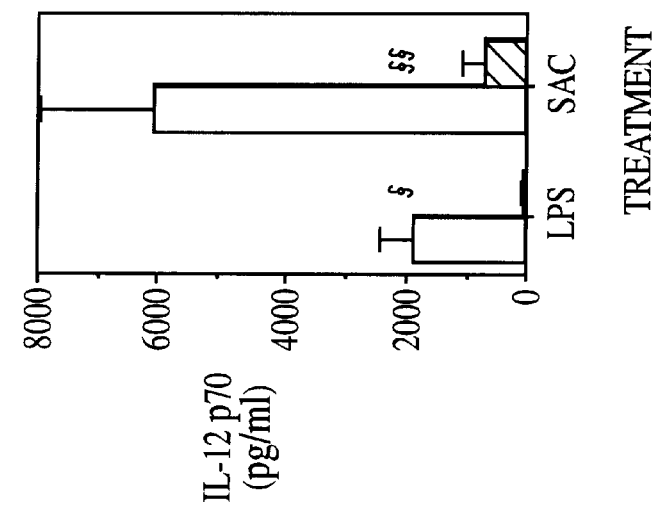
FIG. 4A is a graph illustrating suppression of IL-12 p70 production in human monocytes by GB24. Values shown are means plus standard errors of isotype-treated (white bars) and anti-CD46 treated (black bars) of monocyte cultures (n=3–5). Monocytes were stimulated with IFN-γ plus LPS or SAC as indicated. * P<0.049, ** P=0.003, +P=0.020, ++P=0.024, +§P=0.021 and §§P=0.006.
Figure 4B:
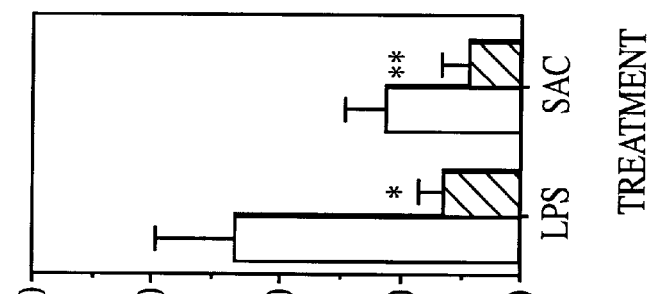
FIG. 4B is a graph similar to that of FIG. 4A depicting suppression of IL-12 p70 production by the anti-CD46 ligand, TRA-2-10. Symbols are as indicated in the description of FIG. 4A.
Figure 4C:
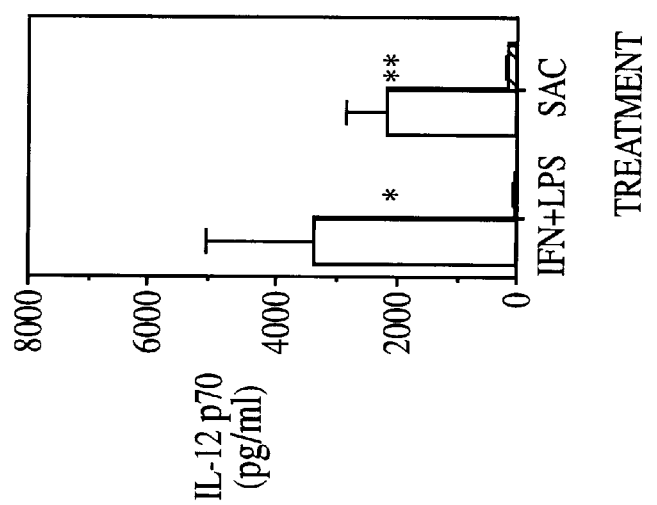
FIG. 4C is a graph similar to that of FIG. 4A depicting suppression of IL-12 p70 production by the anti-CD46 ligand, J4-48. Symbols are as indicated in the description of FIG. 4A.
Figure 4E:
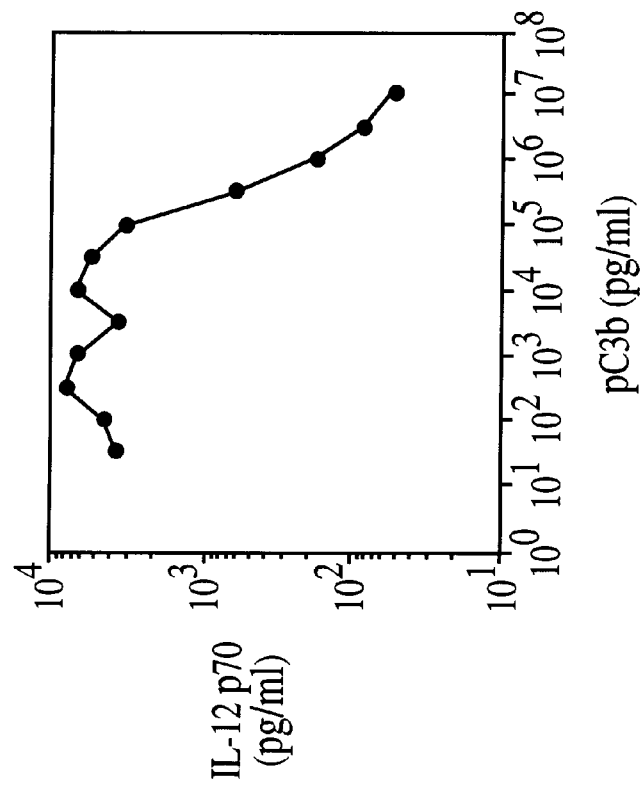
FIG. 4E is a dose response curve of pC3b-mediated suppression of IL-12 production by monocytes prior to stimulation with IFN-γ/SAC.
Figure 4D:
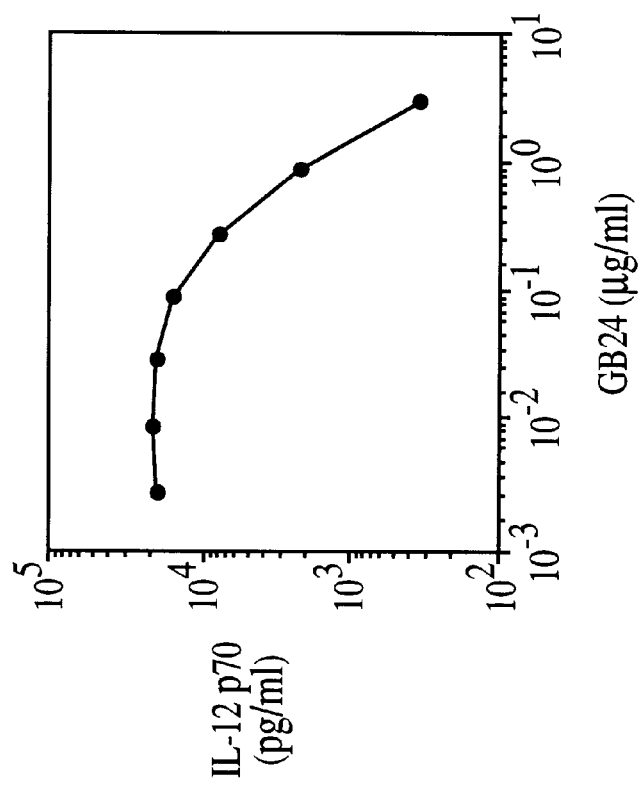
FIG. 4D is a dose response curve of GB24-mediated suppression of IL-12 production following stimulation with IFN-γ/SAC.

To determine whether endogenous complement ligands for CD46 also affect modulation of immunoregulatory monokine production, monocytes were incubated with ½-log-fold dilutions of dimerized C3b (pC3b) prepared as previously described (Kalli et al., 1991, J. Exp. Med. 174:1451), prior to stimulation with IFI-γ/SAC. The dose-dependent suppression of IL-12 by dimerized C3b is illustrated in FIG. 4E, which depicts the results of one experiment that is representative of a total of three experiments. Treatment of monocytes with pC3b also resulted in a striking, dose-dependent decrease in IL-12 production by monocytes, suggesting that complement activation products can directly regulate the production of IL-12.

A comparable linkage between the complement and acquired immune systems has previously been reported (Fearon et al., 1995, Annu. Rev. Immunol. 13:127). This report discloses cross-linking of CD19, an RCA like CD46, to membrane immunoglobulin (mIg) on B cells, which enhanced B cell activation by dramatically reducing the number of mIg molecules that need to be ligated for activation to occur.

Example 5
Suppression of IL-12 Production at the level of Transcription

The effects of anti-CD46 antibody on IL-12 p40 and p35 mRNA levels in human monocytes was examined. Elutriated human monocytes were cultured in the presence of GB24, a monoclonal anti-CD46 antibody, followed by stimulation with IFN-γ and LPS. Total RNA was isolated and RNase protection assays were performed using human IL-12 p40 and p35 specific riboprobes. The amount of radioactivity present was detected, quantitated, and was normalized against the amount of radioactivity detected using cyclophillin as a probe. The results are expressed either as fg of IL-12 p40 specific mRNA per μg of total RNA, or as accumulated counts in the case of p35 mRNA. The data establish suppression of IL-12 p40 and p35 mRNA production in the presence of anti-CD46 antibody.

A similar experiment was performed wherein the effect of measles virus hemagglutinin on suppression of IL-12 p40 and p35 mRNA production was examined. Elutriated human monocytes were infected with measles virus, or were cultured in the presence of GB24, a monoclonal anti-CD46 antibody. Cells were then stimulated with IFN-γ and LPS and the nuclei were isolated from the cells. Run-on assays were performed in the presence of α-$^{32}$P-UTP and probes comprising human IL-12 p40 and p35 specific cDNAs immobilized on nitrocellulose membranes. β-actin was used as an internal control. The results establish that measles virus hemagglutinin and anti-CD46 antibody served to suppress transcription of IL-12 p40 and p35 in monocytes.

Example 6
Regulation of IL-12 Production by Complement Receptor 3

The data presented herein establish that ligation of certain cell surface molecules results in the inhibition of IL-12 production, in that, cross-linling of CD46 either with antibody or its natural ligand C3b, inhibits production of IL-12. In addition, infection of primary human monocytes with measles virus specifically downregulates IL-12 production but not TNF-α or IL-6, suggesting that IL-12 deficiency may be a key factor in measles virus-induced immunosuppression. These results are the first indication that complement receptors have the potential to regulate IL-12 production, and consequently, have the potential to regulate a cellular immune response. The question as to whether the observed inhibition of L-12 was exclusively related to CD46 or was also related to complement receptor 3 (CR3) was therefore addressed. In these experiments, the role of CR3 in the induction of IL-12 by a variety of the stimuli in an in vitro system using cells of human and murine origin as IL-12 producers was examined.

Figure 8A:
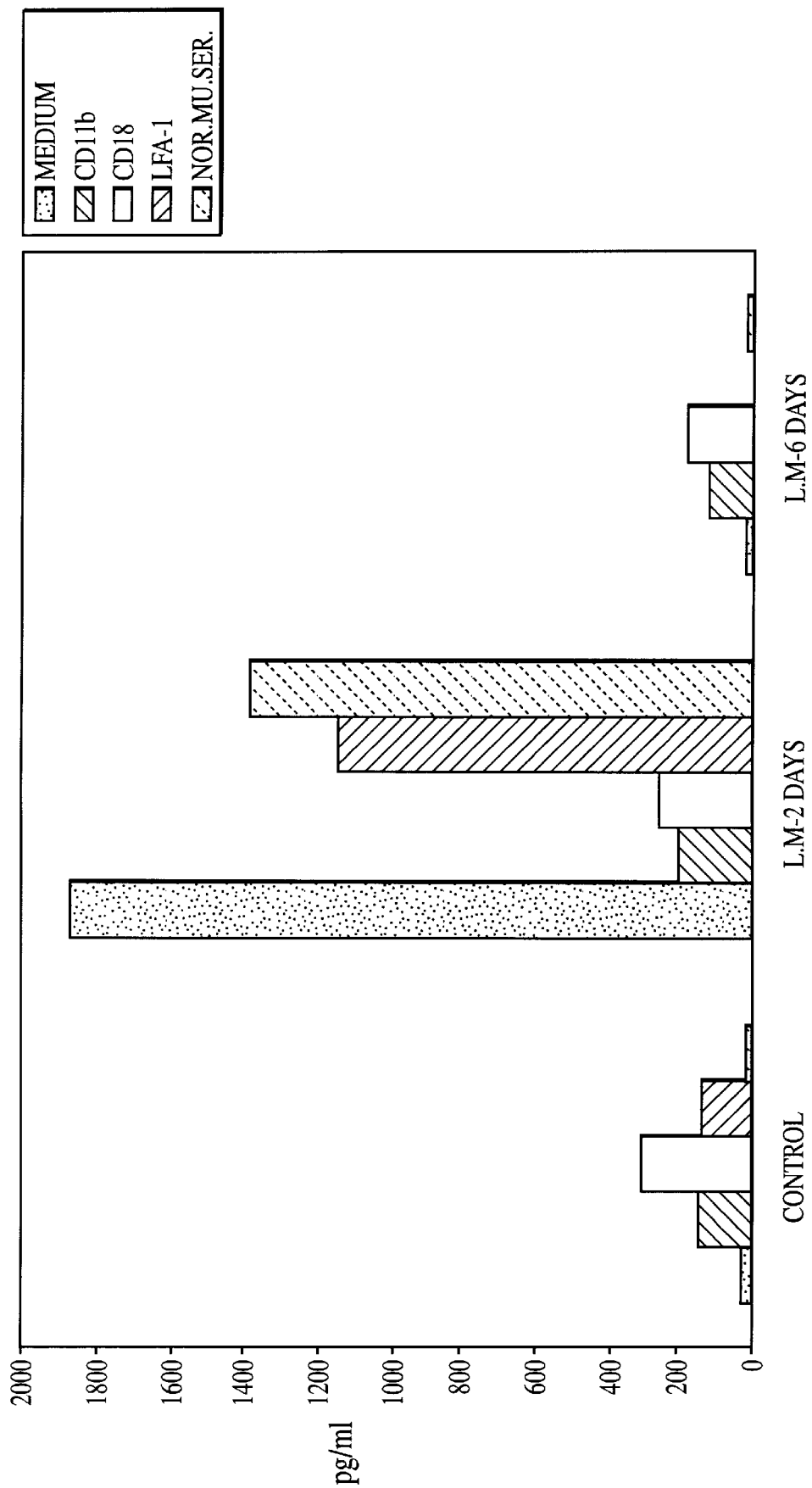
FIG. 8A is a graph depicting the effect of anti-CR3 antibodies on the production of IL-12 p40 by human PBMC stimulated with *Leishmania Major*.
Figure 8B:
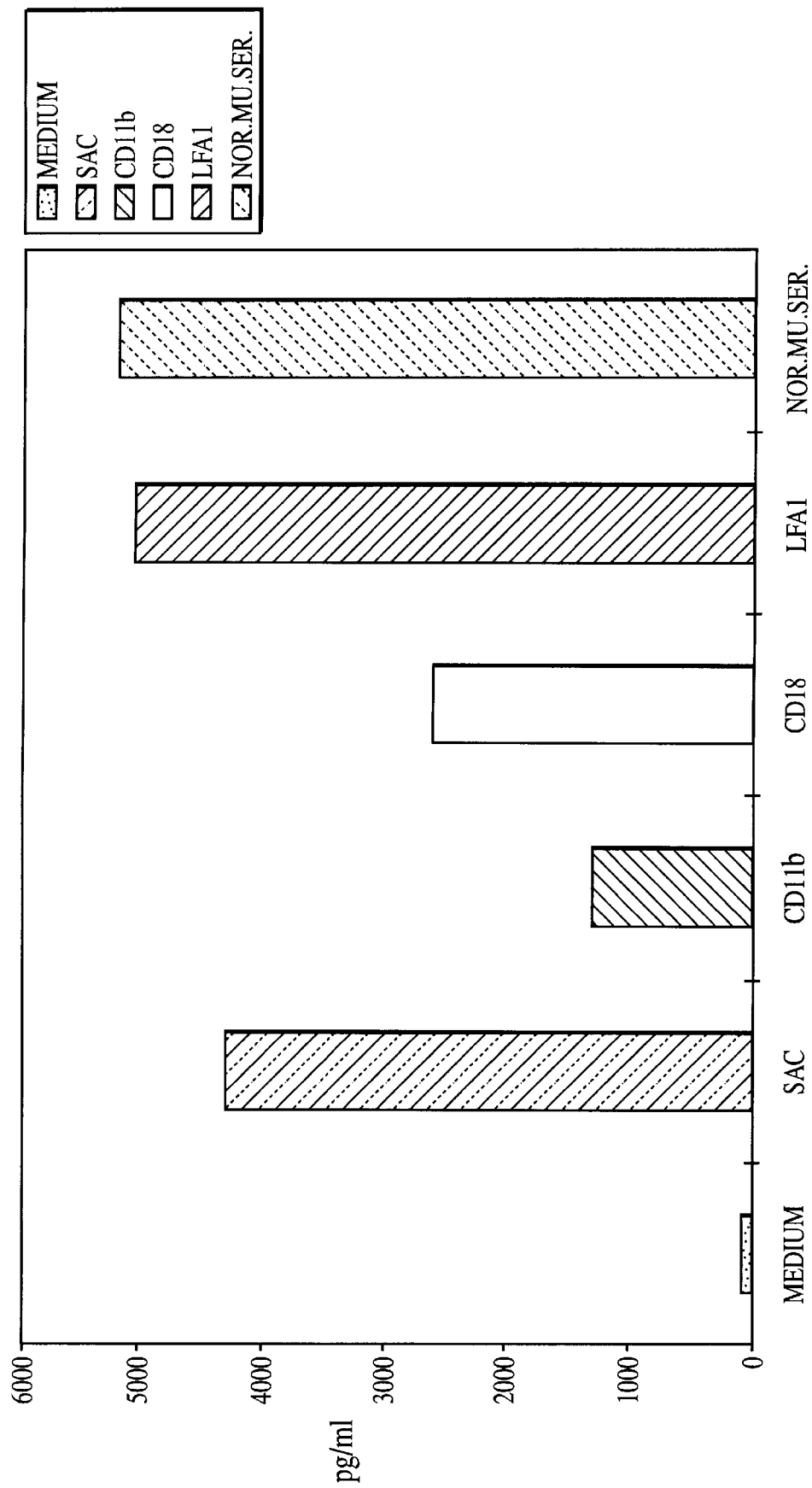
FIG. 8B is a graph depicting the effect of anti-CR3 antibodies on the production of IL-12 by human PBMC stimulated with SAC.

Human PBMC were obtained by Ficoll-Hypaque gradient separation from the peripheral blood of healthy volunteers. A volume (0.9 ml) of cells at the concentration of $2.7 \times 10^6$ cells/ml in RPMI 1640 medium containing 10% FCS was added to 48 well plates. An amount (50 μl) of the following components at the indicated concentrations was then added to the wells: CD11b-OKM1, 20× culture supernatant; CD18-L130-10 μg/ml; LFA-1, ascites, normal mouse serum (nor.mu.ser.) followed by either medium (control), Leishmania major promastigotes at 1:1 cell:parasite ratio (L.M.2 days), Leishmania major mastigotes at 1:1 ratio (L.M. 6 days) (FIG. 8A) or *Staphylococcus aureus* Cowan strain 1 diluted 1:10000 (SAC) (FIG. 8B).

Figure 6:
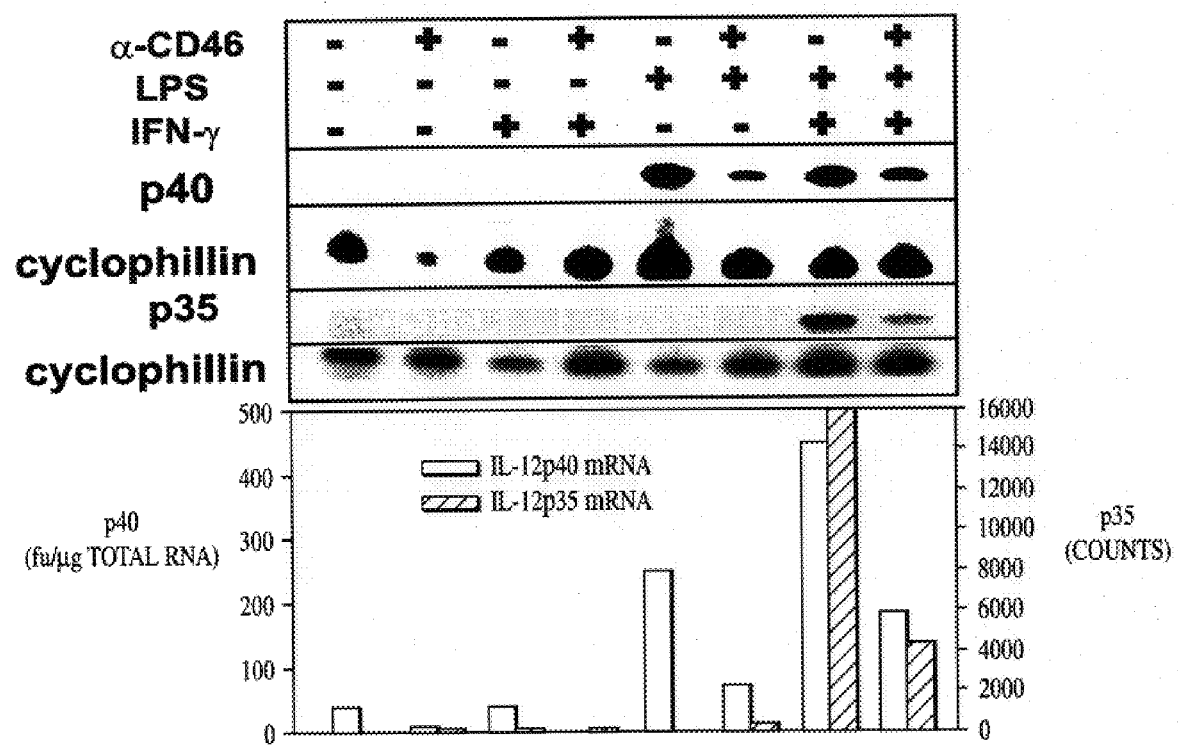
FIG. 6 is an image of a transcription assay depicting the effects of anti-CD46 antibody on IL-12 p40 and p35 mRNA levels in human monocytes.
Figure 7:
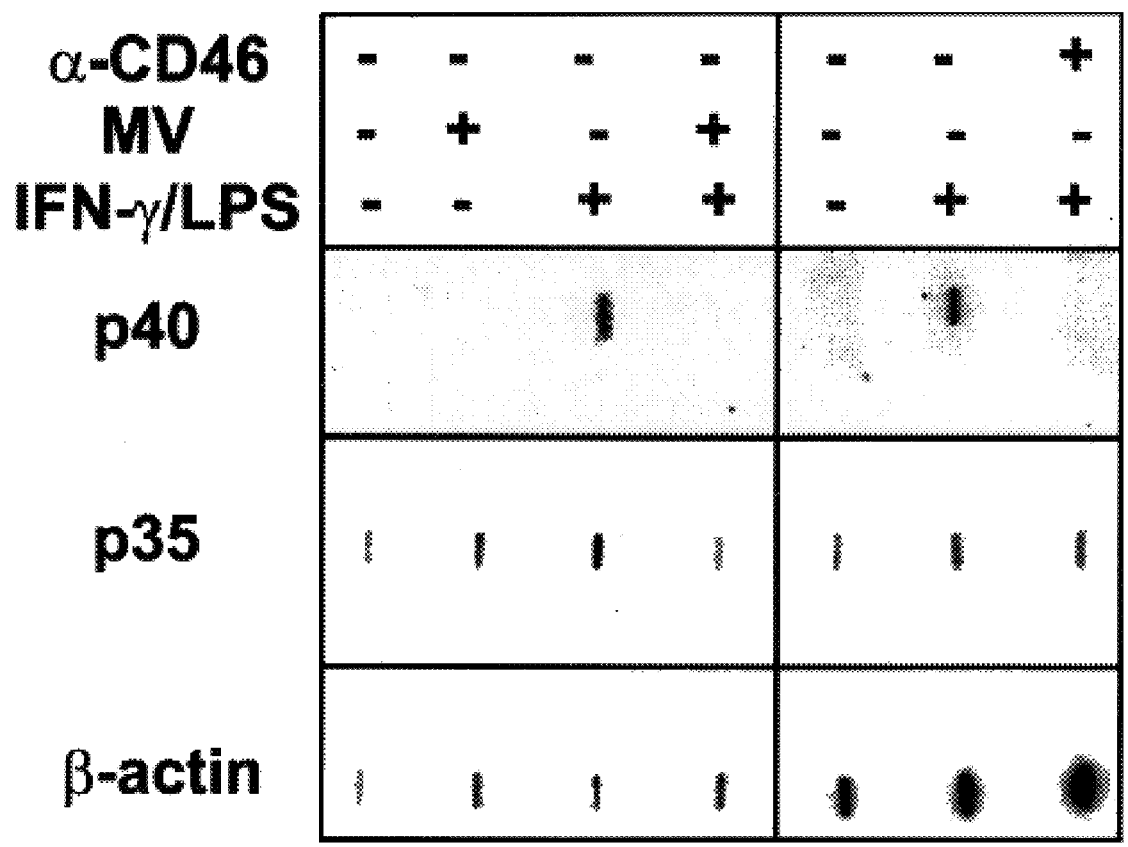
FIG. 7 is an image of a transcription assay depicting the effects of measles virus and anti-CD46 antibody on the transcription of IL-12 p40 and p35 genes.

Twenty four hours later, culture supernatants were harvested and the presence of IL-12 p40 in the supernatants was assessed by radioimmunoassay (RIA). The results are presented in FIGS. 6A and 6B and establish that IL-12 production stimulated by *L. major* promastigotes or by SAC was inhibited by anti CD11b (OKM1) and CD18 (L130 antibody) but not by the anti CD11a (LFA-1).

Figure 9:
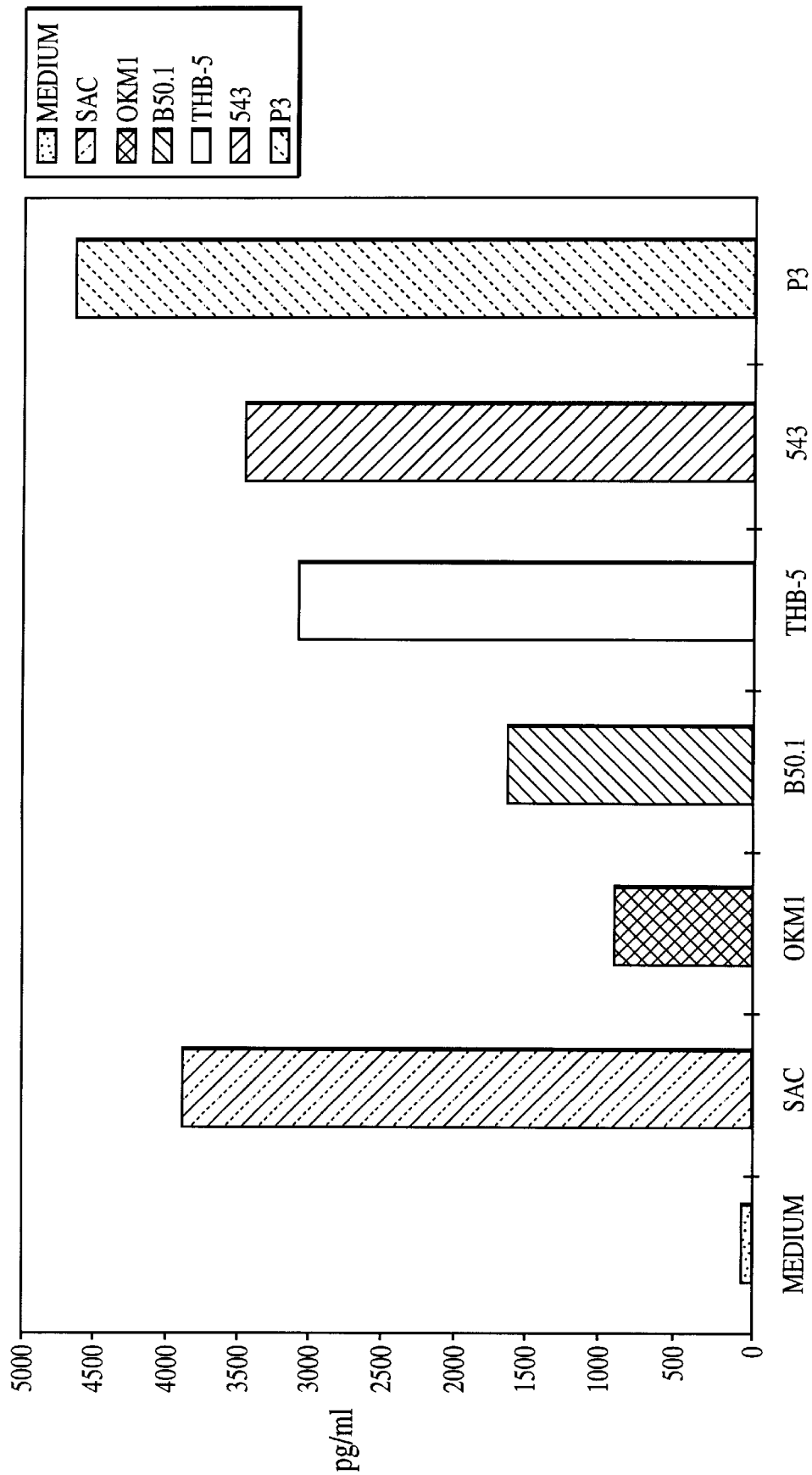
FIG. 9 is a graph depicting the effect of anti-CR3 antibodies on the production of IL-12 by human PBMC stimulated with SAC.

The inhibition of IL-12 production by antibody against CR3 but not against CR1 or CR2 was further confirmed by the data shown in FIG. 9. PBMC which were exposed to SAC for 24 hours in the presence of antibodies against CR3 (OKM1, B50.1) produced significantly less IL-12 p40 than did cells which were exposed to SAC in the presence of control antibody P3 (P×63, murine IgG). In contrast, anti CR1 (Mo543) and anti CR2 (THB-5) antibodies exhibited no significant inhibitory effect on the production of IL-12 as compared with the level of IL-12 produced by SAC stimulation only. All of the antibodies were used in the form of ascites fluid diluted at 1/160).

Figure 10:
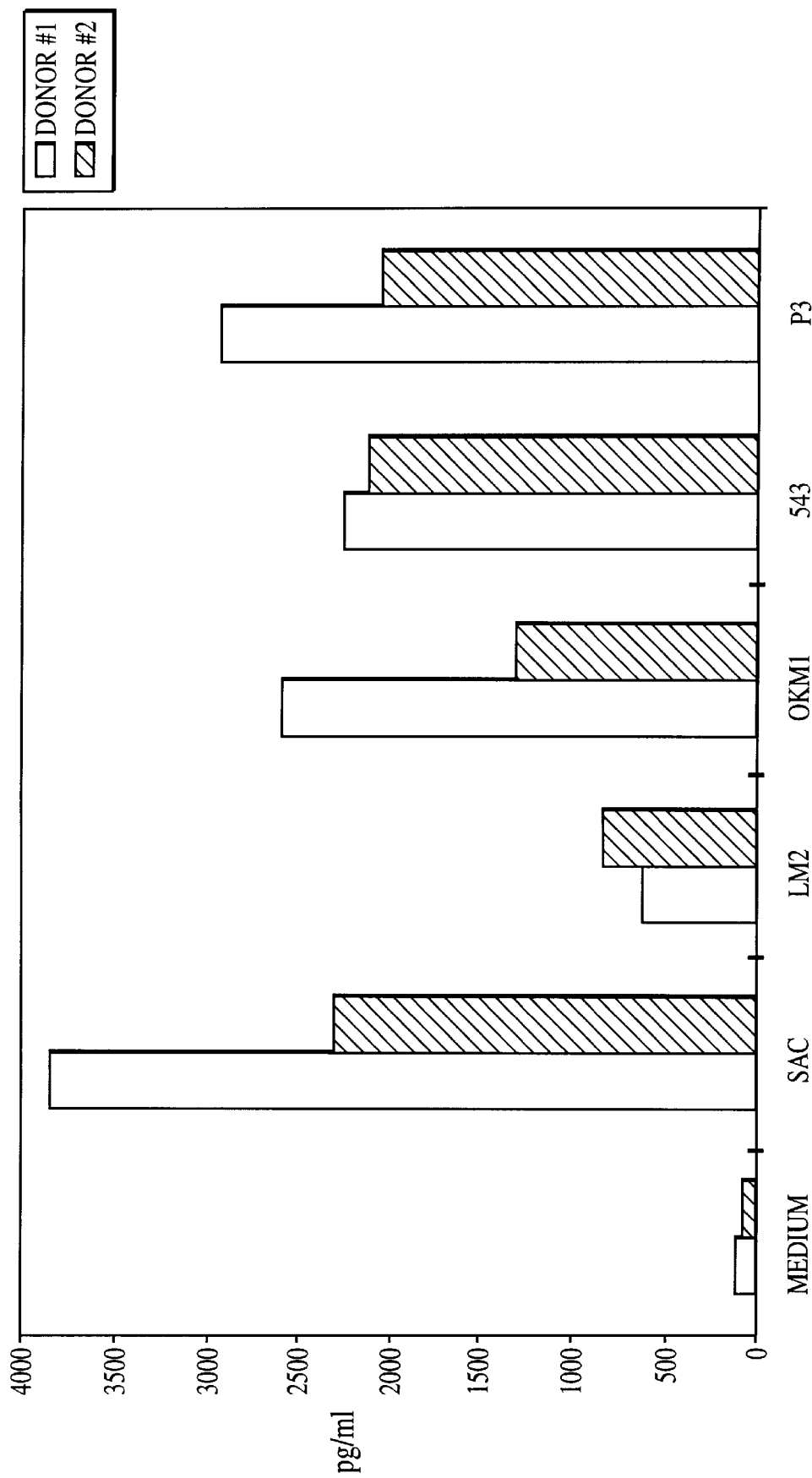
FIG. 10 is a graph depicting the effect of anti-CR3 antibodies on the production of IL-12 p40 by human PBMC stimulated with SAC.

In addition to OKM1 and B50.1, another anti-CR3 CD11b antibody, LM2/1, used at a concentration of 1 μg/ml, exhibited a strong inhibitory effect on the production of IL-12 p40 by PBMC obtained from 2 donors stimulated with SAC (FIG. 10). The OKM1 antibody used at the same concentration exhibited significant inhibition of IL-12 production, but the inhibition was not as profound as that observed previously. The inhibition of IL-12 which was observed in cells obtained from one donor exposed to Mo543 against CR1 was confined to this experiment only.

Figure 11:
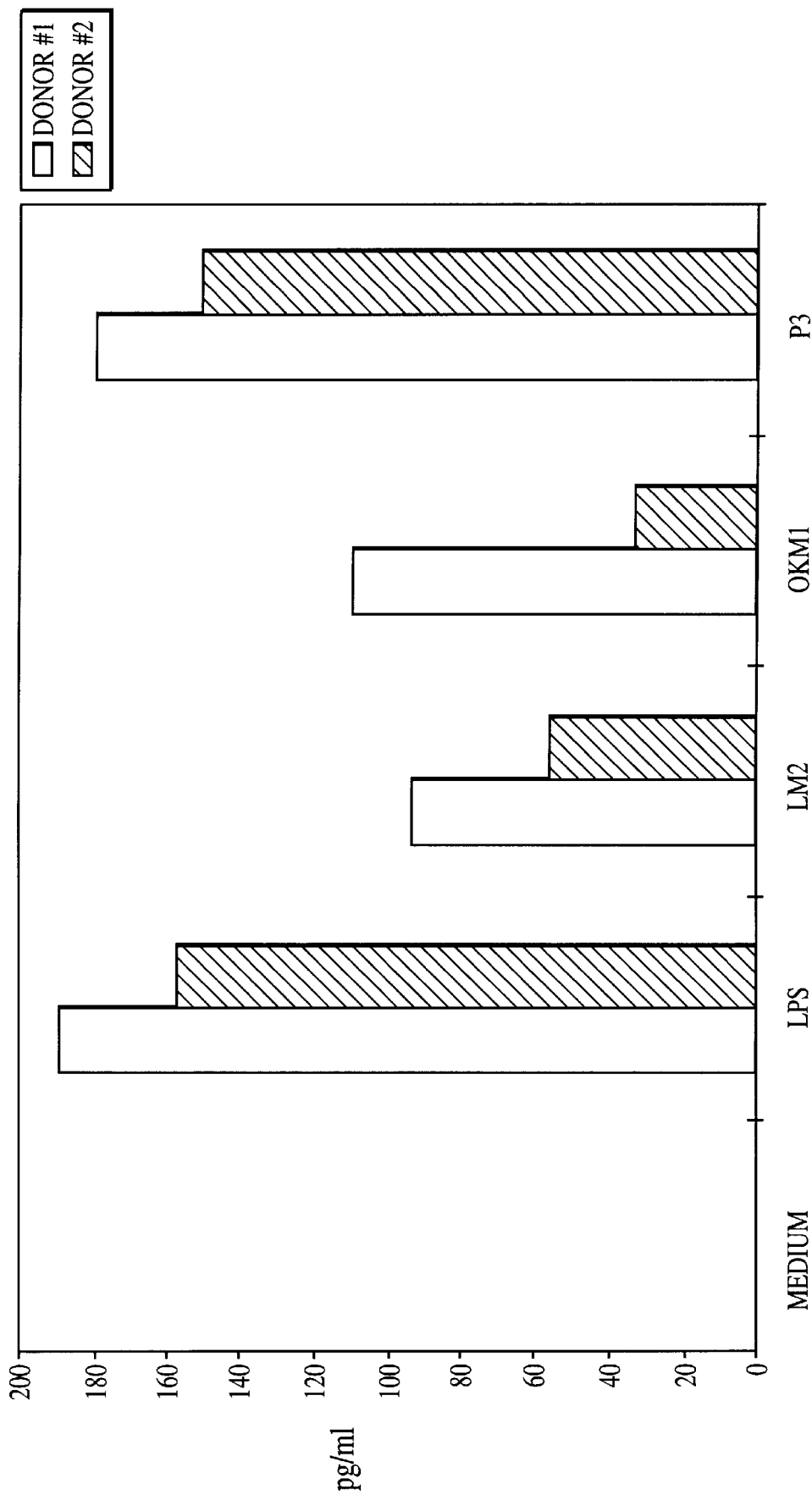
FIG. 11 is a graph depicting the production of IL-12 p40 by human neutrophils exposed to LPS in the presence of anti-CR3 antibodies.

The ability of anti-CR3 antibodies LM2/1 and OKM1, to suppress IL-12 p40 production by human neutrophils exposed to LPS was also examined. Similar to the results obtained using PBMC, IL-12 p40 production by LPS stimulated neutrophils was inhibited by these two antibodies but not by the control antibody P3 (FIG. 11).

Studies extended to an in vivo murine system further confirmed the role of CR3 in the regulation of IL-12 production. Murine elicited peritoneal macrophages were plated in 48 wells plate at a concentration of $1\times10^6$ cells/well. Cells were cultured for 20 hours in the presence of low molecular weight hyaluronan (5 $\mu$g/ml), a natural ligand for CD44, LPS, or SAC, in the presence of different concentrations of the antibody M1/70, directed against MAC-1/CD11bCD18, or in the presence of control antibodies, HB88 anti-murine IgM; MAC-3; normal rat IgG (N. rat); $F(ab')_2$ fragment of normal rat IgG (N. rat Fab).

Figure 12:
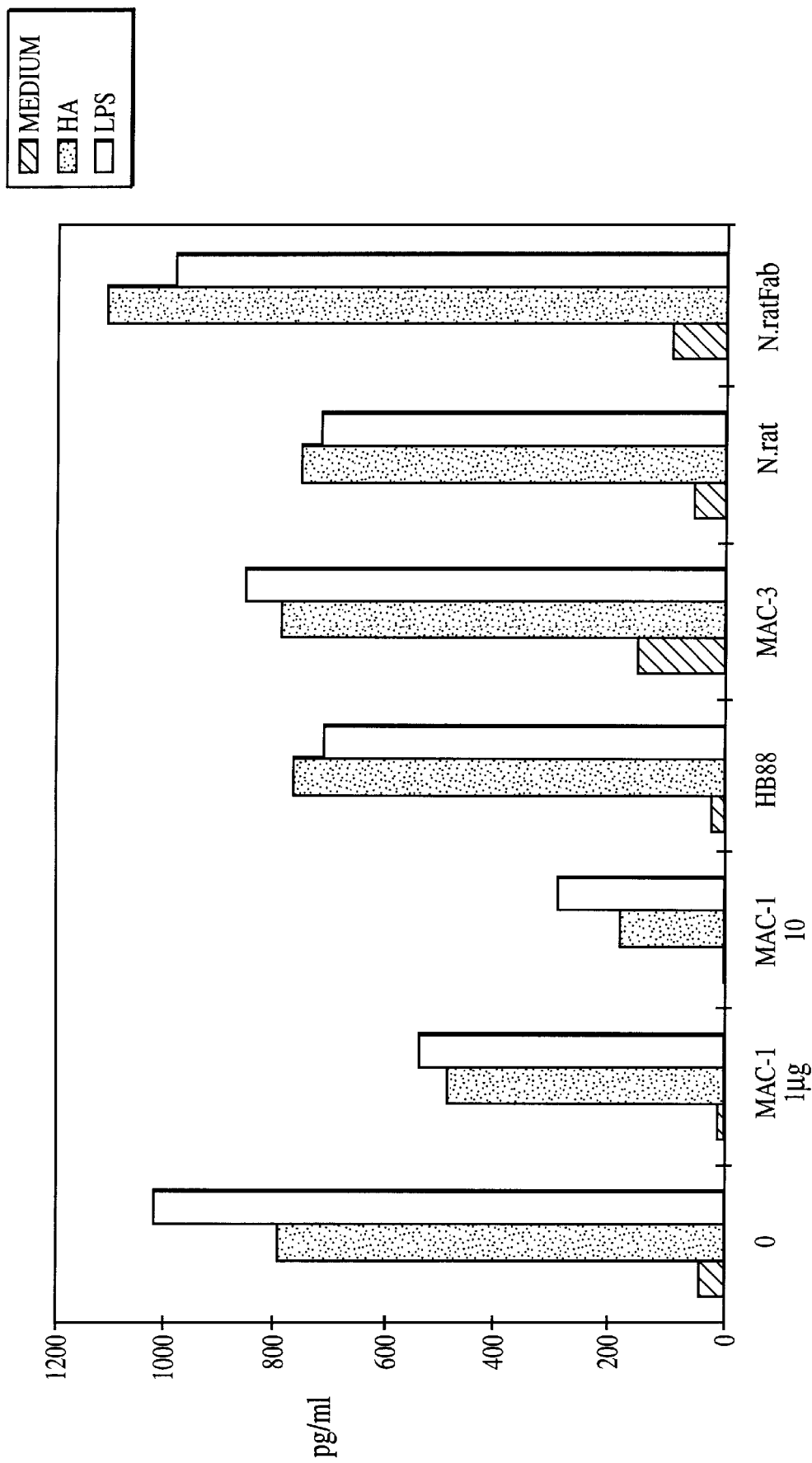
FIG. 12 is a graph depicting the production of IL-12 p40 by thioglycolate-induced murine macrophages stimulated with low molecular weight hyaluronan (HA) and LPS.

Ligation of CD44 with its natural ligand low molecular weight hyaluronan (HA) induced IL-12 production in mice. This production was inhibited, in a dose-dependent manner, by antibody against MAC-1, but not by any of the control antibodies examined (FIG. 12). Induction of I1-12 by LPS was also inhibited by anti MAC-1 antibody when used under these conditions.

Figure 13A:
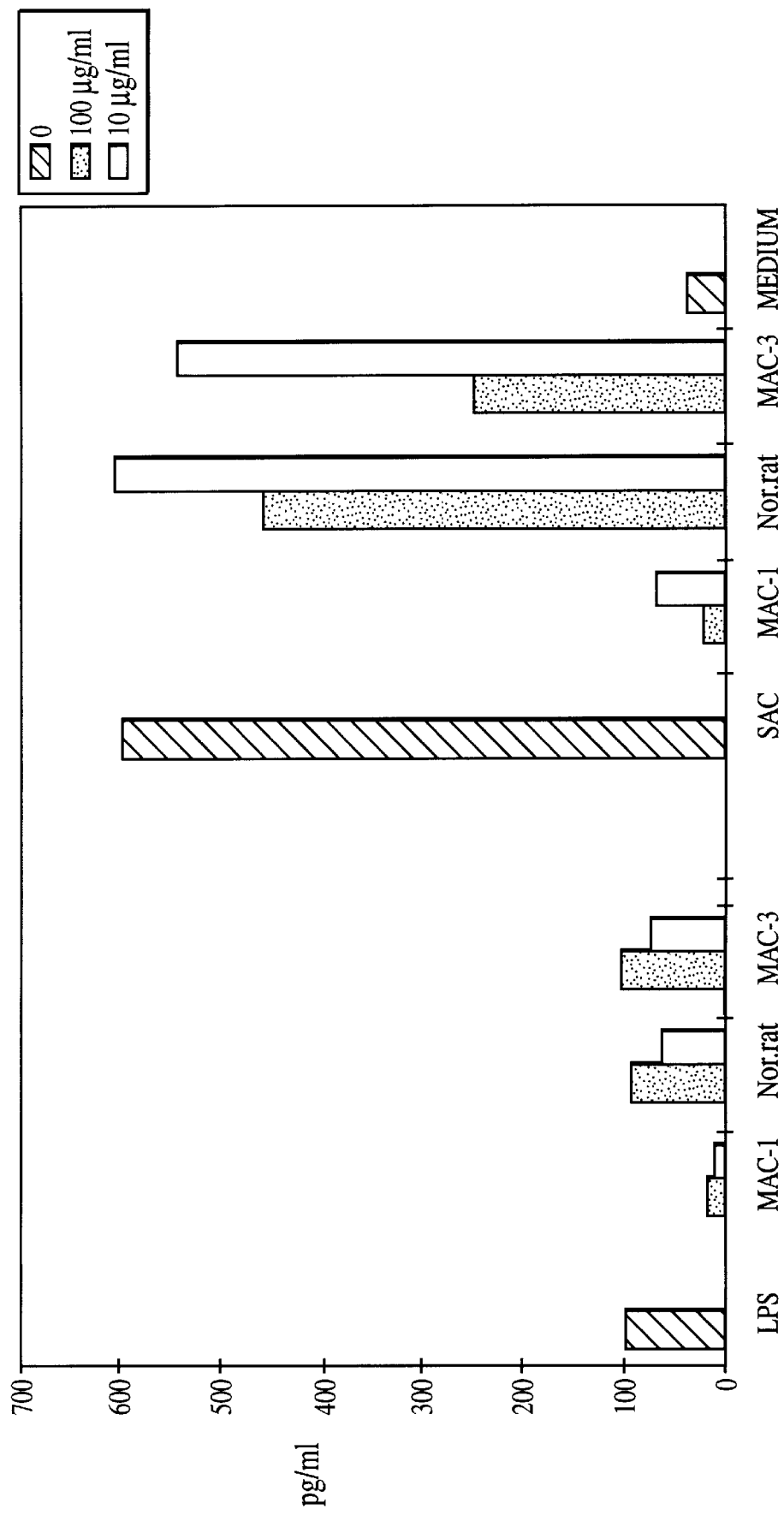
FIG. 13A is a graph depicting the effect of anti-MAC-1 antibody on the production of IL-12 p40 by BALB/c macrophages stimulated with LPS or SAC.
Figure 13B:
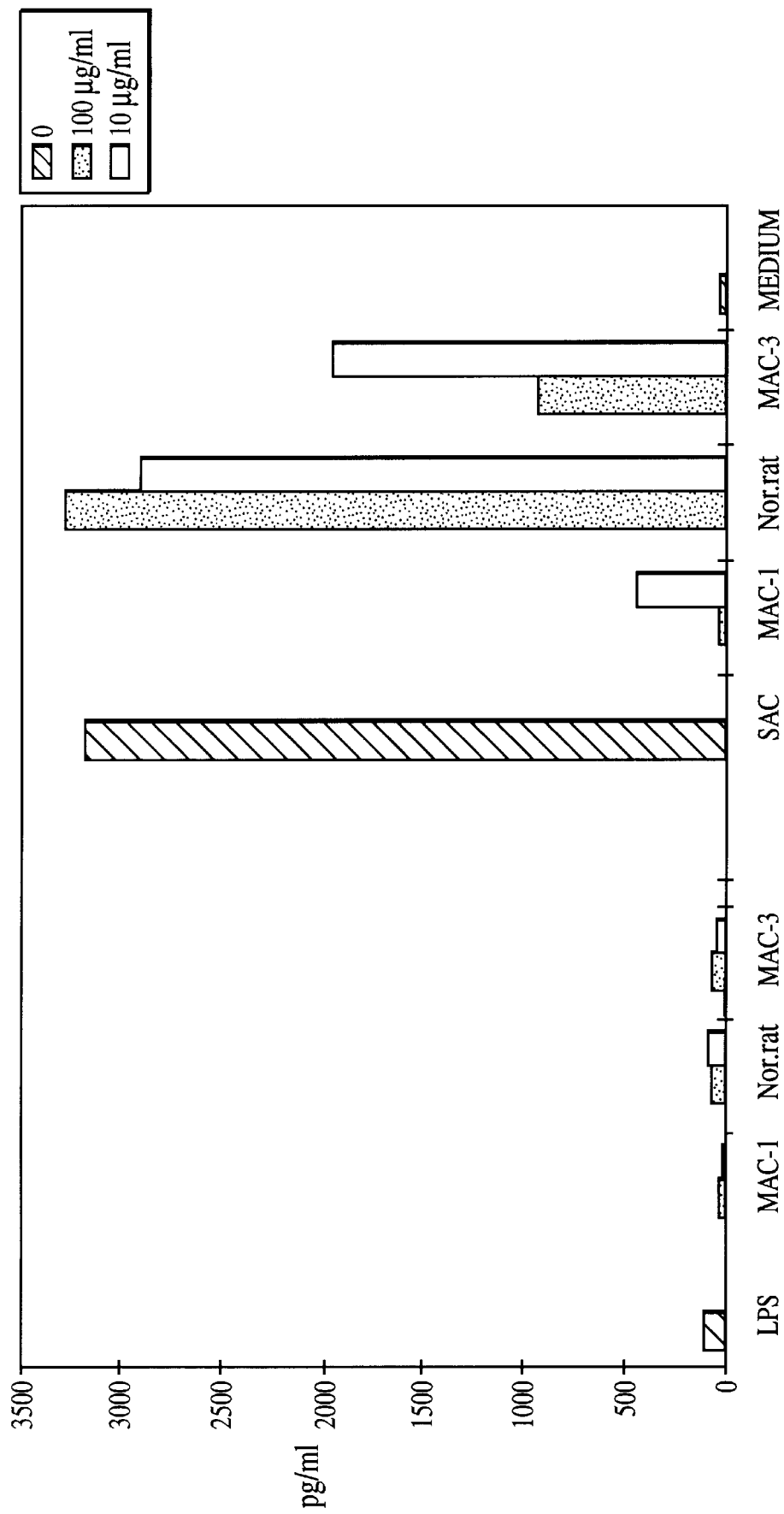
FIG. 13B is a graph depicting the effect of anti-MAC-1 antibody on the production of IL-12 p40 by C3H/HeN macrophages stimulated with LPS or SAC.

Using elicited macrophages obtained from BALB/c and C3H/HeN mice, the fact that IL-12 production can be specifically controlled by anti-CR3 antibodies was confirmed. These data establish therefore, that anti-CR3 antibodies are capable of selectively suppressing IL-12 production. In addition, the observed inhibition of IL-12 production was not the result of an unspecific effect of antibody on the producer cells, since the antibody directed against another macrophage surface molecule, MAC-3, did not exhibit any inhibitory activity of IL-12 production (FIG. 13A, FIG. 13B).

These data obtained from both mouse and human systems, despite the observed variability among human donors, strongly suggest that CR3 ligation has the ability to regulate IL-12 production and, that CR3, working via IL-12, mediates cellular inunune responses generated during the infection.

The disclosures of each and every patent, patent application and publication cited herein are hereby incorporated herein by reference in their entirety. Particularly, Karp et al., 1996, Science 273:228–231, is incorporated herein by reference.

While this invention has been disclosed with reference to specific embodiment, it is apparent that other dembodiments and variations of this invention may be devised by other skilled in the art without departing from the true spirit and scope of the invention. The appended claims are intended to be construed to include all such embodiments and equivalent variations.

What is claimed is:

1. A method of suppressing IL-12 production in a human in need of such suppression, said method comprising administering to said human a ligand that binds the complement receptor protein CD46, wherein said ligand is suspended in a pharmaceutically acceptable carrier and said binding suppresses IL-12 production.

2. The method of claim 1, wherein said ligand is an isolated protein or an isolated polypeptide.

3. The method of claim 2, wherein said ligand is selected from the group consisting of a polyclonal antibody, a monoclonal antibody, a synthetic antibody, a chimeric antibody and a humanized antibody.

4. The method of claim 1, wherein said ligand is selected from the group consisting of an anti-CD46 antibody, C3b, C4b, and measles virus hemagglutinin.

5. The method of claim 4, wherein said ligand is an anti-CD46 antibody.

6. The method of claim 1, wherein said human is afflicted with a disease that is accompanied by pathological delayed-type hypersensitivity responses.

7. The method of claim 6, wherein said disease is an organ-specific autoimmune disease.

8. The method of claim 6, wherein said disease is selected from the group consisting of rheumatoid arthritis, multiple sclerosis, graft-versus-host disease, diabetes mellitus, sarcoidosis, granulomatous colitis, systemic lupus erythematosus and Crohn's disease.

9. The method of claim 1, wherein said ligand is administered to the human in an amount between about 1 nglkg and about 100 mg/kg of patient body weight.

10. The method of claim 1, wherein said ligand is administered to said human in an amount between about 15 micrograms to about 80 micrograms of ligand per kg of patient body weight.

11. The method of claim 1, wherein said pharmaceutically acceptable carrier is physiological saline.

12. A method of suppressing IL-12 production in a cell, said method comprising administering to said cell a ligand that binds the complement receptor protein CD46, wherein said binding suppresses IL-12 production.

* * * * *